United States Patent [19]
Bonner et al.

[11] Patent Number: 5,902,331
[45] Date of Patent: May 11, 1999

[54] ARRANGEMENT FOR IMPLANTING AN ENDOCARDIAL CARDIAC LEAD

[75] Inventors: Matthew D. Bonner, Plymouth; Timothy G. Laske, Shoreview, both of Minn.

[73] Assignee: Medtronic, Inc., Minneapolis, Minn.

[21] Appl. No.: 09/037,654

[22] Filed: Mar. 10, 1998

[51] Int. Cl.$^6$ ................................................. A61M 25/01
[52] U.S. Cl. ......................... 607/122; 600/585; 606/129
[58] Field of Search .................................. 607/116, 119, 607/122; 600/585; 606/129

[56] References Cited

U.S. PATENT DOCUMENTS

| | | |
|---|---|---|
| 3,348,548 | 10/1967 | Cardack . |
| 3,788,329 | 1/1974 | Friedman . |
| 4,646,755 | 3/1987 | Kane . |
| 4,876,109 | 10/1989 | Mayer et al. . |
| 4,972,847 | 11/1990 | Dutcher et al. . |
| 5,003,990 | 4/1991 | Osypka . |
| 5,007,435 | 4/1991 | Doan et al. . |
| 5,036,854 | 8/1991 | Schollmeyer et al. . |
| 5,046,497 | 9/1991 | Millar . |
| 5,139,033 | 8/1992 | Everett et al. . |
| 5,246,014 | 9/1993 | Williams et al. . |
| 5,257,974 | 11/1993 | Cox ........................................... 600/585 |
| 5,304,218 | 4/1994 | Alferness . |
| 5,531,783 | 7/1996 | Giele et al. . |
| 5,545,200 | 8/1996 | West et al. . |

Primary Examiner—William E. Kamm
Assistant Examiner—George R. Evanisko
Attorney, Agent, or Firm—Reed A. Duthler; Harold R. Patton

[57] ABSTRACT

An arrangement for introducing and implanting the electrode(s) of an endocardial implantable cardiac lead at a cardiac implantation site within a heart chamber or vessel. An elongated guide body formed of flexible material and extending between a guide body proximal end and a guide body distal end is advanced transvenously to position the guide body distal end in relation to the cardiac implantation site. A guide body tracking mechanism is coupled with the lead distal end for receiving and slidingly engaging the guide body to allow the cardiac lead to be advanced along the guide body until the electrode is positioned at the cardiac implantation site. Pusher mechanism formed of an elongated pusher body of flexible material extends between a pusher body proximal end and a pusher body distal end and has a cardiac lead engaging mechanism for engaging the cardiac lead at or adjacent the distal lead end. The pusher body has sufficient column strength to be advanced alongside the guide body and lead body with the cardiac lead engaging mechanism engaging and slidingly advancing the guide body tracking mechanism and the cardiac lead distally along the guide body to thereby allow the cardiac lead to be advanced along the guide body until the electrode is positioned at the cardiac implantation site. The lead body is released from the lead engaging mechanism and fixed, if the lead includes a fixation mechanism. The pusher mechanism is retracted by retraction of the pusher body.

7 Claims, 14 Drawing Sheets

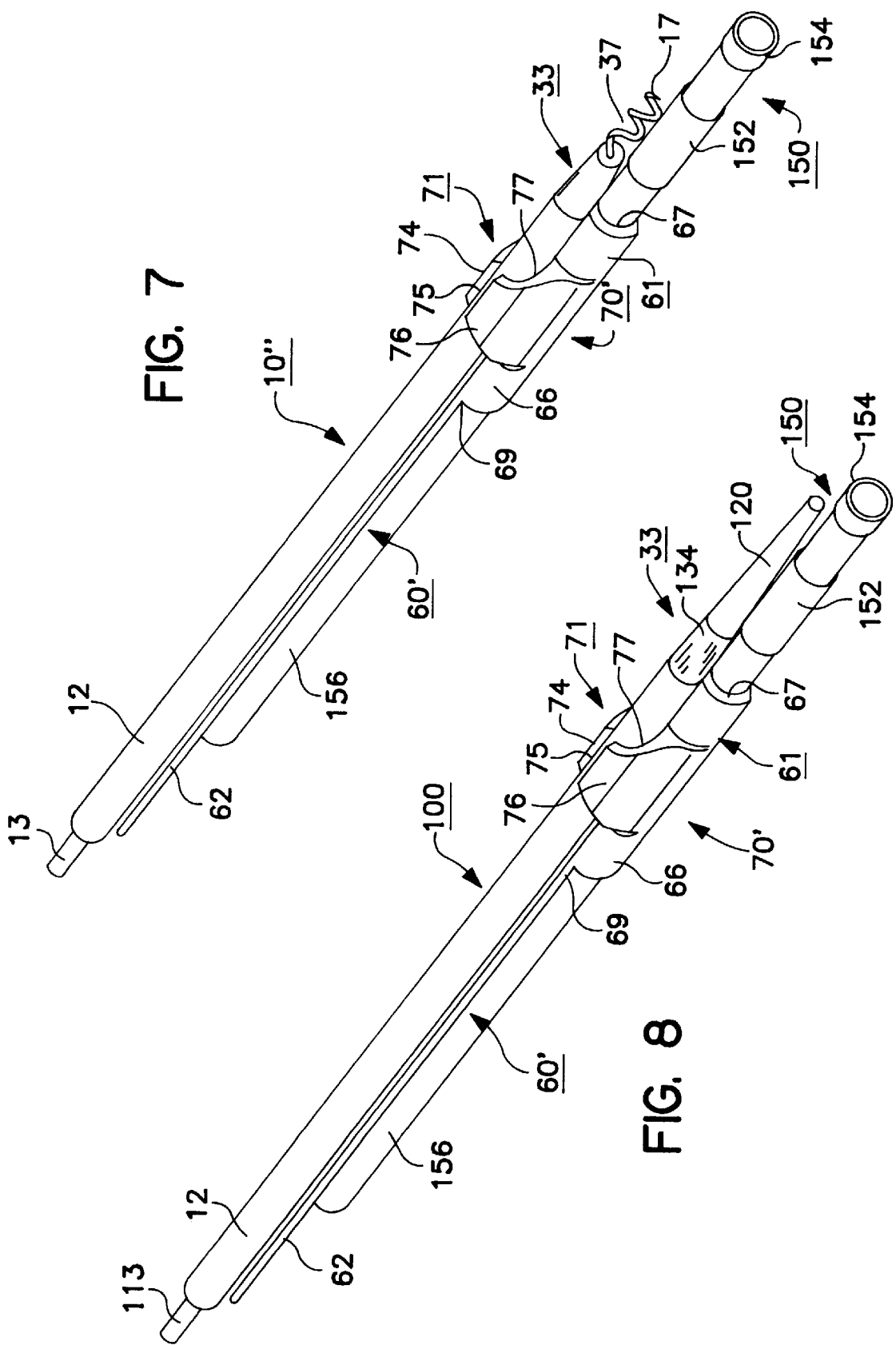

ARRANGEMENT FOR IMPLANTING AN ENDOCARDIAL CARDIAC LEAD

FIELD OF THE INVENTION

The present invention relates to endocardial implantable cardiac leads for applying electrical stimulation to and/or sensing electrical activity of the heart at one or more electrode positioned at a cardiac implantation site within a heart chamber or cardiac vessel adjacent a heart chamber and more particularly to an arrangement for transvenously introducing and fixing the electrode at the implantation site.

BACKGROUND OF THE INVENTION

Implantable medical electrical stimulation and/or sensing leads are well known in the fields of cardiac stimulation and monitoring, including cardiac pacing and cardioversion/defibrillation, and in other fields of electrical stimulation or monitoring of electrical signals or other physiologic parameters. In the field of cardiac stimulation and monitoring, endocardial leads are placed through a transvenous route to locate one or more sensing and/or stimulation electrode along or at the distal end of the lead in a desired location in a chamber of the heart or a blood vessel of the heart. In order to achieve reliable sensing of the cardiac electrogram and/or to apply stimulation that effectively paces or cardioverts the heart chamber, it is necessary to accurately position the electrode surface against the endocardium or within the myocardium at the desired site and fix it during an acute post-operative phase until fibrous tissue growth occurs.

The pacemaker or defibrillator implantable pulse generator (IPG) or the monitor is typically coupled to the heart through one or more of such endocardial leads. The proximal end of such leads typically is formed with a connector which connects to a terminal of the IPG or monitor. The lead body typically comprises one or more insulated conductive wire surrounded by an insulating outer sleeve. Each conductive wire couples a proximal lead connector element with a distal stimulation and/or sensing electrode. An endocardial cardiac lead having a single stimulation and/or sensing electrode at the lead distal end and a single conductive wire is referred to as a unipolar lead. An endocardial cardiac lead having two or more stimulation and/or sensing electrodes at the lead distal end and two or more conductive wires is referred to as a bipolar lead or a multi-polar lead, respectively.

In order to implant an endocardial lead within a heart chamber, a transvenous approach is utilized wherein the lead is inserted into and passed through the subclavian, jugular, or cephalic vein and through the superior vena cava into the right atrium or ventricle. An active or passive fixation mechanism is incorporated into the distal end of the endocardial lead and deployed to maintain the distal end electrode in contact with the endocardium position. Considerable effort has been undertaken to develop electrode passive and active fixation mechanisms that are simple to use and are reliable. Passive fixation mechanisms do not invade the myocardium but cooperate with cardiac tissue or structures to locate the electrode against the endocardium. The most successful passive fixation mechanism comprises a plurality of soft, pliant tines that bear against cardiac structure surfaces, e.g. the trabeculae in the right ventricle and the atrial appendage, to urge the distal tip electrode against the endocardium. Active fixation mechanisms are designed to penetrate the endocardial surface and lodge in the myocardium without perforating through the epicardium or into an adjoining chamber. The most widely used active fixation mechanism employs a sharpened helix, which typically also constitutes the distal tip electrode. Typically, some sort of shroud or retraction mechanism is provided to shield the helix during the transvenous advancement into the desired heart chamber from which the helix can be advanced and rotated when the desired site is reached to effect a penetrating, screw-in fixation. In one manner or another, the helix is adapted to be rotated by some means from the proximal end of the lead outside the body in order to screw the helix into the myocardium and permanently fix the electrode.

More recently, endocardial pacing and cardioversion/defibrillation leads have been developed that are adapted to be advanced into the coronary sinus and coronary veins branching therefrom in order to locate the distal electrode(s) adjacent to the left ventricle or the left atrium. The distal end of such coronary sinus leads is advanced through the superior vena cava, the right atrium, the valve of the coronary sinus, the coronary sinus, and into a coronary vein communicating with the coronary sinus, such as the great vein. Typically, coronary sinus leads do not employ any fixation mechanism and instead rely on the close confinement within these vessels to maintain each electrode at a desired site.

The heart beats approximately 100,000 times per day or over 30 million times a year, and each beat stresses at least the distal end portion of the lead. Over the years of implantation, the lead conductors and insulation are subjected to cumulative mechanical stresses, as well as material reactions as described below, that can result in degradation of the insulation or fractures of the lead conductors with untoward effects on device performance and patient well being. The endocardial lead body is subjected to continuous stretching and flexing as the heart contracts and relaxes and is formed to be highly flexible and durable. It is necessary to temporarily stiffen the lead conductor sire to advance the lead through these blood vessels and to locate the distal electrode(s) at the desired site.

Early implantable, endocardial and epicardial, bipolar cardiac pacing leads of the type disclosed in U.S. Pat. No. 3,348,548 placed the separate coiled wire conductors in a side by side configuration and incorporated a lumen for receiving a stiffening stylet inside the lumen of at least one of the conductor coils. This design was replaced by a coaxial configuration of the type shown in U.S. Pat. No. 3,788,329 wherein the separate coiled wire conductors are wound in differing diameters separated from one another by tubular insulating sheaths and extend coaxially about a central lumen for receiving the stiffening stylet. The stiffening wire or stylet is advanced through a proximal connector pin opening to stiffen the lead body during the transvenous introduction. Most current endocardial cardiac leads employ multi-filar, parallel-wound, coiled wire conductors electrically connected in common in an electrically redundant fashion as a single polarity lead conductor in each of the unipolar, bipolar and multi-polar lead configurations. Such redundant coiled wire conductors of bipolar and multi-polar lead bodies are coaxially arranged about the stiffening stylet receiving lumen and insulated from one another by coaxially arranged insulating sheaths separating each coiled wire conductor from the adjacent coiled wire conductor(s).

In the implantation of a cardiac device of the types listed above, and in the replacement of previously implanted cardiac leads, two or more transvenous cardiac leads are typically introduced through the venous system into the right chambers or coronary sinus of the heart. It has long been desired to minimize the diameter of the transvenous cardiac lead body to facilitate the introduction of several cardiac leads by the same transvenous approach. Moreover, a number of multi-polar, endocardial cardiac leads have been designed to accommodate more than two electrodes or to make electrical connection with other components, e.g., blood pressure sensors, temperature sensors, pH sensors, or the like, in the distal portion of the lead. The increased number of separate polarity coiled wire conductors is difficult to accommodate in the conventional coaxial coiled wire conductor winding arrangement employing tubular insulating sheaths to separate the coil wire conductors of differing diameters having a desired overall lead body outer diameter.

This need for increased numbers of lead conductors in the lead body has led to the development of separately insulated, coiled wire conductors that are parallel-wound with a common diameter and are separately coupled between a proximal connector element and to a distal electrode or terminal in the manner described in commonly assigned U.S. Pat. No. 5,007,435, for example. The coaxial construction technique may also be combined with the parallel-winding technique to multiply the total number of separate coiled wire conductors accommodated within a specified endocardial lead body outer diameter.

All of the above considerations as to the complexity of the leads, the number of leads implanted in a common path and the advancement of coronary sinus leads deep in the coronary veins have led to efforts to at least not increase and optimally to decrease the overall diameter of the cardiac lead body without sacrificing reliability and usability. More recently, it has been proposed to diminish the lead body further by eliminating the lumen for receiving the stiffening stylet and by replacing the coiled wire conductor with highly conductive stranded filament wires or cables. In bipolar or multi-polar leads, each such cable extends through a separate lumen of the lead body to maintain electrical isolation. Without the stiffening stylet, it is necessary to resort to use of another mechanism to pass the lead through the vessel paths identified above and to position and fix the distal end electrode of the lead at the desired site in the heart chamber or vessel.

One approach for implantation of such leads is disclosed in commonly assigned U.S. Pat. No. 5,246,014, incorporated herein by reference, that employs a highly flexible, introducer catheter surrounding the lead body and engaging a distal screw-in electrode. The assembly is advanced to the desired site and rotated to screw the distal screw-in electrode into the myocardium of the right atrium or ventricle. The introducer can also be used to direct a cardiac lead into the coronary sinus opening.

One difficulty with use of such an introducer surrounding the cardiac lead is that permanently implantable endocardial leads are formed typically with a proximal connector end assembly having a diameter exceeding that of the lead body and conforming to an industry standard so that the connector end assembly can be fitted into and seal with an IPG connector bore conforming to the same standard. Consequently, the introducer has to be made large enough to fit over the enlarged diameter connector end assembly. This detracts from the ability to advance the introducer and lead assembly through small diameter blood vessels. Or the lead has to be made with a small diameter, non-conforming, connector end assembly or without any connector end assembly and therefore requiring connection to an adapter to be made conforming to the standard. This is inconvenient and can result in a diminished reliability.

Another approach is disclosed in U.S. Pat. No. 5,003,990, also incorporated by reference herein, that relies on a guidewire and a carriage that releasably engages the distal screw-in electrode and is pushed along the guidewire as the lead body is pushed along the transvenous path. The guidewire is first introduced along one of the above-described desired paths, and the carriage engaging the distal electrode is placed over the proximal end of the guidewire and introduced into the blood vessel. Force is exerted against the lead body to push the carriage and the distal end of the lead body distally along the guidewire until the distal electrode is near to the desired site. The guidewire end or a curve in its distal end is engaged by the carriage, and the lead body distal end is bent until the screw-in electrode disengages from the carriage. Then, the carriage is retracted along the guidewire by pulling on another wire attached to the carriage or by the retraction of the guidewire, and the lead body is rotated from the proximal end to screw the helix electrode into the myocardium. Such retraction of the relatively bulky carriage presents the possibility of damage to an artery or vein by the carriage. In addition, releasing the carriage from the guidewire requires the lead or catheter to be bent in the area of the carriage presenting further possibilities of tissue damage during such carriage removal. Still further, once the lead is free of the carriage, its distal end will not necessarily be at its desired final implantation position. Use of the carriage during both implantation of the lead or catheter and retraction of the carriage requires numerous manipulations by the physician which only adds further complexity to an already complex procedure.

In a further approach disclosed in U.S. Pat. No. 5,304,218, incorporated by reference herein, a cardiac lead is formed with a channel in the distal tip that receives a guidewire that has already been advanced through the path to the cardiac implantation site. The lead is pushed over the guidewire to the cardiac implantation site where the guidewire is withdrawn and the lead is either fixed in place or left at the cardiac implantation site. There is no disclosure of how this approach could be used to advance a cardiac lead having an active or passive fixation mechanism at or near the channel in the distal end of the lead body.

Moreover, in both of these approaches, the lead body must possess sufficient column strength to allow it (as well as the carriage of the '990 patent) to be pushed from the proximal end outside the patient's body and along the guidewire. The lead body diameter and/or construction materials that are required in order to make the lead body stiff enough to accomplish this over the wire advancement method necessarily make the lead body larger and less flexible than is desirable to withstand the rigors of chronic flexing as described above. The over the wire approach is classically employed in advancement of balloon catheters for PTCA use which is intended to be of short duration.

Thus, a need remains for an introduction arrangement that allows the introduction of an endocardial cardiac lead having a highly flexible lead body and small lead body diameter into a heart chamber or vein and allowing the use of the active or passive fixation mechanism (if present) at the desired site.

SUMMARY OF THE INVENTION

It is therefore an object of the present invention to provide an introduction arrangement that can be employed to introduce an endocardial cardiac lead that lacks a lumen for receiving a stiffening stylet and lacks sufficient column strength to be pushed to a desired implantation site of a cardiac lead electrode in a heart chamber or cardiac blood vessel without necessarily using a lead introducer.

It is a further object of the invention to provide an apparatus and method that allows introduction of such a lead over a guidewire already advanced to the desired cardiac implantation site.

These and other objects of the invention are realized in an arrangement to facilitate the introduction and advancement of an endocardial cardiac lead through an incision in a patient's skin and a vein and transvenously within the patient's vasculature to position an electrode of the cardiac lead at the cardiac implantation site. The endocardial cardiac lead includes a lead body extending between a lead proximal end and a distal lead end, a lead conductor extending within the lead body between the proximal and distal lead ends, and a cardiac electrode(s) at or adjacent the lead distal end electrically conducted to the lead conductor and may include a distal fixation mechanism. The arrangement for advancement of the cardiac lead preferably comprises elongated guiding means for guiding the transvenous introduction and advancement of the endocardial lead to position the electrode at the cardiac implantation site and comprising an elongated flexible guide body extending between a guide body proximal end and a guide body distal end and capable of being advanced transvenously to position the guide body distal end in relation to a cardiac implantation site, and pusher means formed of an elongated pusher body for advancing the cardiac lead transvenously alongside the guide body. The elongated pusher body is formed of flexible material extending between a pusher body proximal end and a pusher body distal end having sufficient column strength to be advanced over the guidewire and to pull the cardiac lead alongside the pusher body by manipulation of the pusher body proximal end outside the incision in the patient's body.

The pusher means further comprises guide body tracking means coupled with the pusher body distal end for receiving and slidingly engaging the guide body as the pusher body proximal end is advanced, and cardiac lead engaging means for engaging a feature of the cardiac lead at or adjacent the lead distal end and coupled with the guide body tracking means to allow the cardiac lead to be advanced with advancement of the guide body tracking means along the guide body as the pusher body proximal end is advanced until the electrode is positioned at the cardiac implantation site.

In one embodiment, the guide body tracking means and the cardiac lead engaging means are both coupled with the pusher body distal end so that the advancement of the pusher body proximal end advances the guide body tracking means over the guide body and advances the cardiac lead engaged in the cardiac lead engaging means alongside the guide body. In a variation of the first embodiment, the guide body tracking means loosely engages the guide body and the cardiac lead engaging means loosely encircles the lead body and bears against a feature, e.g. a shoulder or fixation mechanism of the lead body adjacent the lead distal end to advance it distally. In this variation, the guide body tracking means and the cardiac lead engaging means can comprise guide body tracking and lead body receiving loops or cylinders attached side by side to the distal end of the pusher body. The lead body receiving loop or cylinder surrounds a lead body receiving lumen that preferably can be provided with an opening or breech that can be opened to allow the lead body between the proximal lead connector end assembly and the lead distal end to pass through it and can be closed to retain the lead body in the lead body receiving lumen. The guide body tracking loop or cylinder surrounds a guide body tracking lumen into which the guide body distal end can be inserted or withdrawn.

During advancement of the cardiac lead to the cardiac implantation site, the guide body tracking loop or cylinder is advanced distally over the guide body, and the lead body receiving loop or cylinder bears against the feature adjacent the distal lead end. The abutment of the lead body receiving loop or cylinder against the feature prevents it from passing over the lead distal end and applies force to it to pull the cardiac lead along during advancement of the pusher body to locate the cardiac electrode at the cardiac implantation site accessed by the guiding means. After the fixation mechanism, if any, is deployed, the pusher body proximal end is withdrawn proximally. The guide body tracking loop or cylinder is retracted proximally over the guide body and the lead body receiving loop or cylinder is retracted proximally over the lead body until they are withdrawn from the incision, where the arrangement can be disassembled.

In a second embodiment, the cardiac lead engaging means comprises a feature, e.g. a lead engaging loop, formed at the lead distal end having a guide body engaging lumen for receiving and slidingly engaging the guide body to allow the lead distal end to be advanced over the guide body. In this case, the guide body tracking means is a guide body tracking loop or cylinder attached to the pusher body distal end that fits over the guide body and can be advanced distally or retracted proximally by manipulation of the pusher body proximal end outside the incision in the patient's skin. During advancement, the guide body tracking loop engages the lead engaging loop and slidingly advances the lead distal end distally along the guide body upon advancement of the pusher body to thereby allow the cardiac lead to be advanced alongside the guide body until the electrode is positioned at the cardiac implantation site. Then, the guide body and pusher body including the guide body tracking loop are retracted proximally through the patient's vasculature and incisions. Preferably, the lead engaging loop is formed of a flexible loop of resorbable material extending outwardly of the lead body that dissolves within the patient's body within a predetermined time following implantation that is sufficiently long to allow the implantation of the cardiac lead to be completed.

In these embodiments, the elongated guiding means can simply comprise a conventional guidewire of any known type formed of flexible material and extending between a guidewire proximal end and a guidewire distal end that is capable of being advanced to the cardiac implantation site by manipulation of the guidewire from outside the incision. The guidewire body constitutes the guide body inserted into the guide body tracking lumen of the first and second embodiments and the guide body engaging lumen of the second embodiment. Of course, the elongated guiding means can comprise more complex catheter like structures that are capable of accessing the cardiac implantation site.

In a variation of the first embodiment, the cardiac lead engaging means and the guide body tracking means are integrally attached with the pusher body distal end. The cardiac lead engaging means comprises a lead body receiving loop or cylinder surrounding the lead body receiving lumen that is operable between a clamped state that grasps the lead body and a released state that releases the lead body. In the normal, clamped state, the diameter of the lead body receiving lumen is sized to tightly grasp the lead body adjacent to the distal lead end. In the released state, the diameter of the lead body receiving lumen is expanded, allowing the lead body receiving lumen or cylinder to be advanced or retracted over the lead body. The tight grasp in the clamped state allows the application of rotational torque to the lead body through rotation of the arrangement at the proximal ends of the pusher body, the cardiac lead and the guide body extending outside the incision in the patient's skin. This embodiment further includes release enabling means operable from outside the incision in the patient's skin for operating the cardiac lead engaging means in the released state to release the cardiac lead and to enable transvenous retraction of the pusher means after the cardiac lead is advanced to position the electrode at the cardiac implantation site.

Preferably, in order to expand the lead body receiving lumen, it further comprises an elongated lead breach extending between the proximal and distal guide body tracking lumen end openings normally having a narrow breach width in the clamped state to prevent the lead body from passing therethrough. The lead breach is capable of being widened in the released state to a wide breach width to thereby increase the diameter of the lead body receiving lumen enough to allow it to be withdrawn distally over the lead body. Or the lead breach can be widened sufficiently to allow the lead body to pass laterally through it.

Various mechanisms can be used to selectively operate the cardiac lead engaging means in the released state. In a preferred embodiment, the cardiac lead engaging means and the guide body tracking means are formed of a unitary structure having a living hinge mechanism that provides for the expansion of the diameter of the cardiac lead engaging lumen upon expansion of the diameter of the guide body tracking lumen. The expansion of the guide body tracking lumen is selectively effected when the lead distal end is fully advanced to position the cardiac electrode and deploy the fixation mechanism, if present, at the cardiac implantation site.

Preferably, the selective expansion is effected by inflating a miniaturized balloon on the distal end of a micro-catheter located within the guide body tracking lumen. In this embodiment, the elongated guiding means comprises an elongated micro-catheter having a catheter body extending between a catheter body distal end and a catheter body proximal end, and having the inflatable balloon at the catheter body distal end. A balloon inflation lumen extends between the catheter body proximal end and the inflatable balloon through which inflation fluid is passed from and to the catheter body proximal end for selectively inflating and deflating the balloon. The balloon micro-catheter can also contain a guidewire lumen for advancing it over a guidewire previously extended to the cardiac implantation site.

Thus, in the practice of this embodiment, the micro-catheter body is fitted into the guide body tracking lumen and the lead body is fitted into the lead body receiving lumen of the lead body engaging means before or after the balloon micro-catheter is through the incisions in the patient's skin and the exposed vein and advanced all or part of the way to the cardiac implantation site. The micro-catheter distal end is advanced to the cardiac implantation site. The integral guide body tracking means and lead body engaging means gripping the lead body are advanced over the micro-catheter body by force applied to the pusher body proximal end to pull the cardiac lead along and locate the cardiac electrode at the cardiac site. When the guide body tracking means abuts the micro-catheter body distal end, the inflatable balloon is located within the guide body tracking lumen. The tight grip of the cardiac lead engaging means enables the arrangement to be twisted or rotated from the proximal end thereof to position the cardiac electrode precisely at the cardiac implantation site and to deploy the fixation mechanism, if present. For example, if the cardiac lead is equipped with an active fixation helix, the helix tip can be lodged into the endocardium sufficiently by such manipulation to hold it there as the cardiac lead is released, so that the lead body can then be rotated to screw it into the endocardium. Or the entire arrangement can be rotated from the proximal ends of the pusher body, the micro-catheter and the cardiac lead extending outside the incisions to rotate it into the endocardium.

In any of these cases, the balloon is then inflated to expand the guide body tracking lumen and the lead body receiving lumen and thereby releasing the lead body. The lead body either is preferably released laterally through the lead breach so that the balloon can then be deflated to ease withdrawal through the vasculature and incisions. Alternatively, the lead body can be loosely retained within the lead body receiving lumen in the released state and the assembly of the inflated balloon and the guide body tracking means and the lead engaging means can be withdrawn distally over the lead body through the vasculature and incisions and released from the lead body outside the patient's body.

Each of these embodiments can also be augmented by and practiced with an elongated introducer catheter formed of flexible material having an introducer lumen and extending between a introducer lumen proximal end opening and a introducer lumen distal end opening. The introducer lumen has a lumen diameter sized to receive the cardiac lead, the guidewire and the pusher means in side by side relation. Such an introducer catheter can be employed particularly to introduce the arrangement through the skin incision and the incision in the vein, and may be advanced further through the vasculature to make it easier to traverse bends and narrowed sections thereof. The introducer catheter can also be advanced along the predetermined transvenous path within the vasculature to position the introducer lumen distal end opening in relation to a cardiac implantation site.

Preferably, the cardiac implantation sites include the right atrium, the right ventricle, the coronary sinus and/or the great vein descending from the coronary sinus. The cardiac lead can include an active or passive fixation mechanism formed at the lead distal end adapted to be operated to fix the electrode at the cardiac implantation site.

The arrangement of the present invention advantageously provides a simplified apparatus for and method of introducing endocardial cardiac leads which lack a lumen for receiving a stiffening stylet and lack sufficient column strength to be pushed to a desired cardiac implantation site.

In addition, in certain embodiments, the pusher means can be retracted while the guidewire is left in place in the event that it is necessary to reposition the endocardial lead electrode at the implantation site.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 7 is a partial perspective view of an introduction arrangement employing the combined guide body tracking and cardiac lead engaging means of FIG. 5 for selectively gripping the lead body of an endocardial screw-in lead during advancement over the guide body to the cardiac implantation sites of FIG. 1 and a release mechanism usable therewith;

FIG. 8 is a partial perspective view of an introduction arrangement employing the combined guide body tracking and cardiac lead engaging means of FIG. 5 for selectively gripping the lead body of an endocardial coronary sinus lead during advancement over the guide body to the cardiac implantation sites of FIG. 2 and a release mechanism usable therewith;

Figure 1:
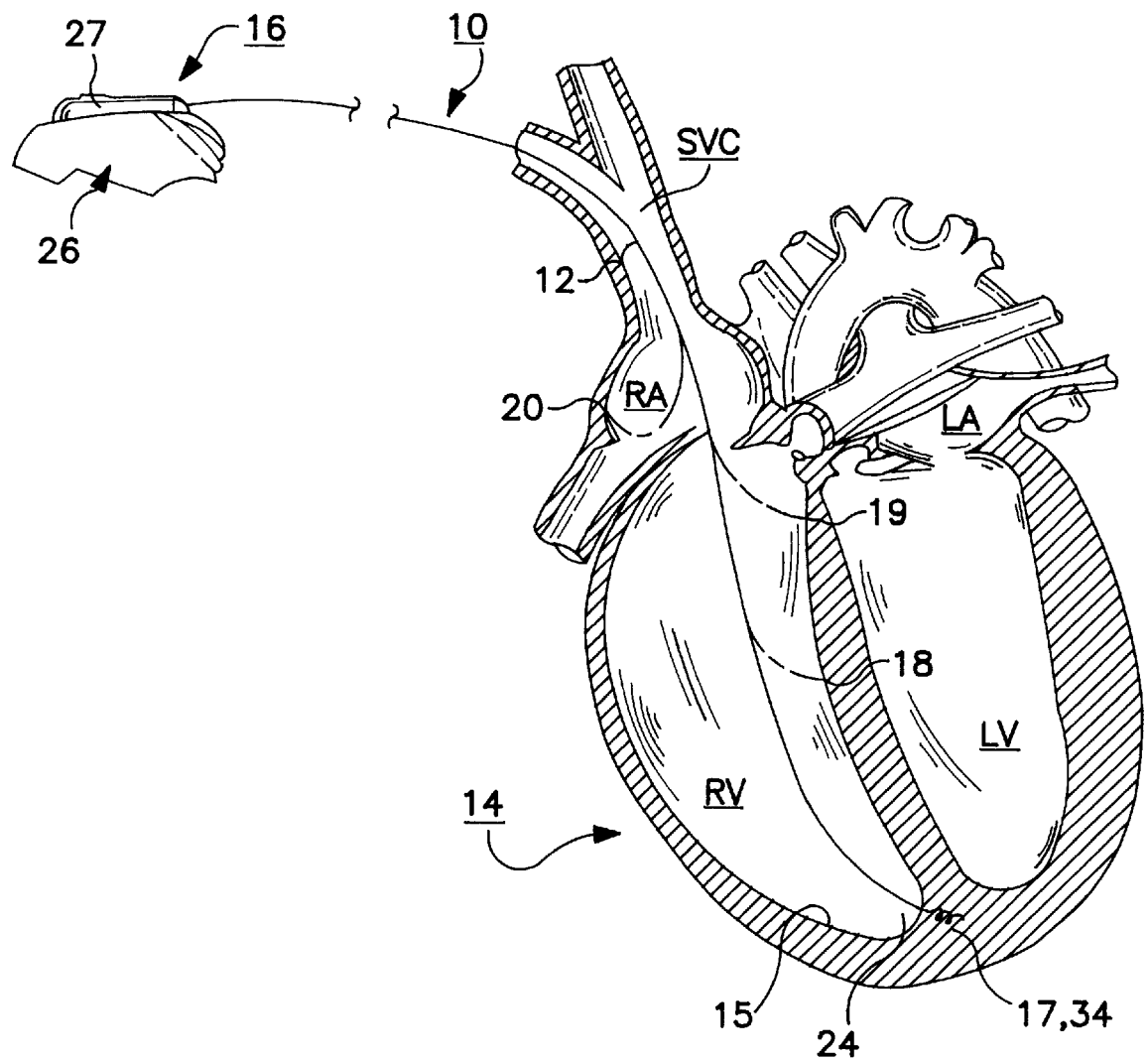
FIG. 1 is a schematic representation of a right heart endocardial cardiac lead bearing at least one cardiac electrode introduced into one of several illustrated cardiac implantation sites of the right heart chambers and coupled at the proximal lead connector end to an implantable medical device.

The drawing figures are not necessarily to scale.

DETAILED DESCRIPTION OF THE PREFERRED EMBODIMENTS OF THE INVENTION

In the following detailed description, references are made to illustrative embodiments for carrying out the invention. It is understood that other embodiments may be utilized without departing from the scope of the invention. The invention and its preferred embodiment may be implemented in unipolar, bipolar or multi-polar, endocardial, cardiac pacing or monitoring leads having one or more pace/sense electrode(s) or sense electrode(s), respectively, at or adjacent the distal lead end. Similarly, the invention and its preferred embodiment may be implemented in endocardial cardiac defibrillation/cardioversion leads including at least one cardioversion/defibrillation electrode and optionally including one or more pace/sense electrode(s) at or adjacent the distal lead end. Moreover, other sensors for sensing a physiologic parameter may be incorporated into the lead body. Each such pace/sense electrode, sense electrode, cardioversion/defibrillation electrode and sensor is coupled with an insulated electrical conductor extending proximally through the lead body to a lead proximal end connector assembly. The proximal connector end assembly is adapted to be coupled to the connector assembly of an implantable or external medical device, including an external or implantable pulse generator (IPG) for pacing, cardioversion/defibrillation or both or an external or implantable monitor. Therefore, it will be understood that the arrangement for introduction of an endocardial cardiac lead of the present invention can be employed to introduce permanently implantable and temporary cardiac leads of these types.

The arrangement of the present invention is particularly useful in introducing such endocardial cardiac leads which are quite small in lead body diameter and are so flexible and possess such low column strength that the lead distal end cannot be advanced transvenously and positioned at the desired implantation site without assistance. Moreover, one particular use of the arrangement of the present invention is to introduce such endocardial cardiac leads that are formed using stranded wire conductor(s) within a lead body diameter of about 0.010–0.026 inches of the type described in the above-incorporated, commonly assigned, '014 patent. The lead body outer diameter is minimized by use of such conductors and by eliminating the lumen for receiving a stiffening stylet. However, the arrangement of the present invention can also be employed to introduce endocardial cardiac leads that employ coiled wire conductors with or without a lumen for receiving a stiffening stylet. In the latter case, the stiffening stylet need not be used to achieve the introduction.

Figure 2:
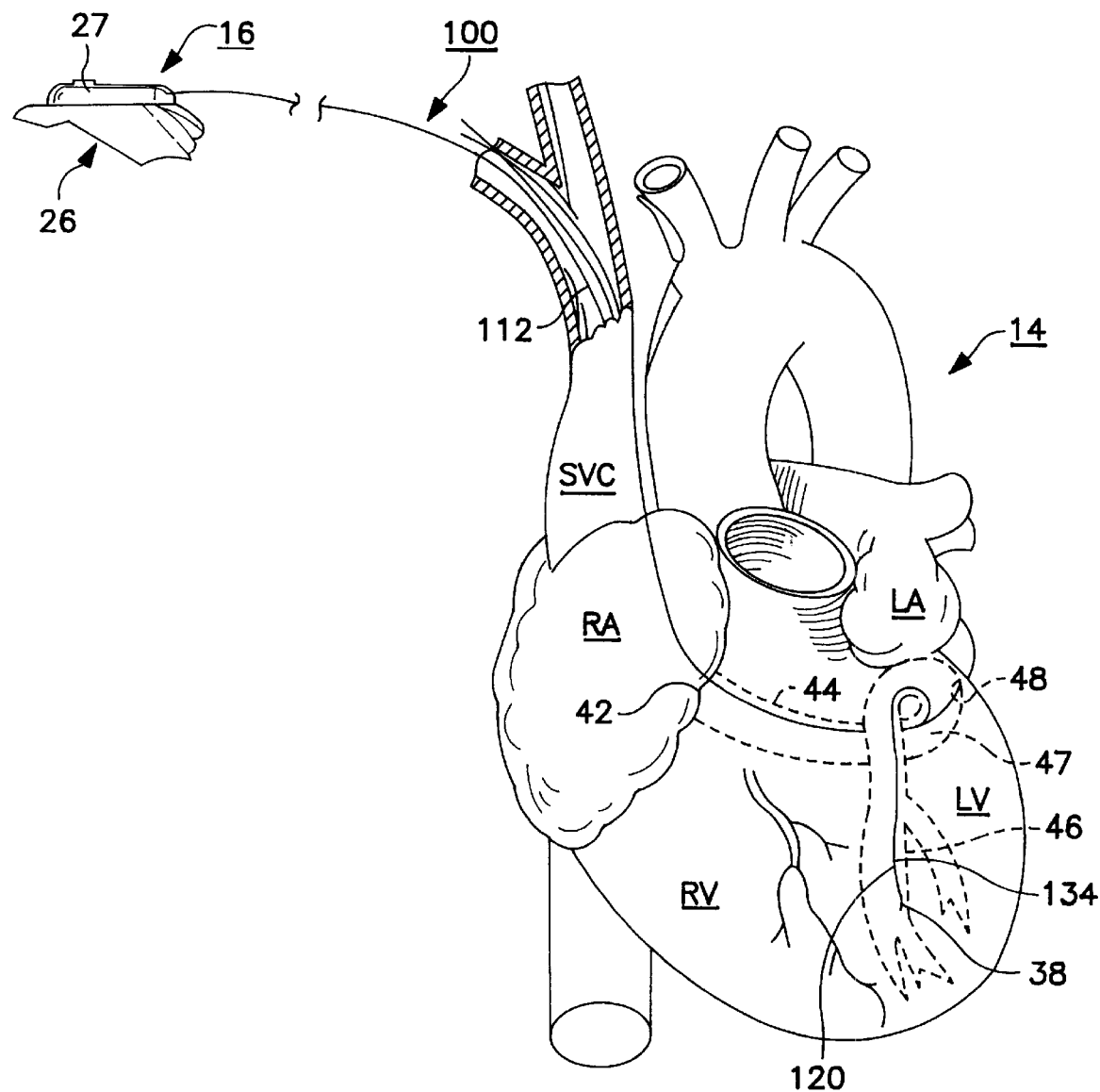
FIG. 2 is a schematic representation of a coronary sinus endocardial cardiac lead bearing at least one cardiac electrode introduced into one possible cardiac implantation sites within the great vein adjacent to left heart chambers and coupled at the proximal lead connector end to an implantable medical device.

FIGS. 1 and 2 are schematic representations of types of right heart cardiac leads 10 (including 10' and 10" described below) and coronary sinus (CS) leads 100 bearing such electrodes introduced into cardiac implantation sites in cardiac blood vessels or chambers of the heart 14 and coupled in each instance at the proximal lead connector ends to an implantable medical device (IMD) 16 of any of the above noted types. In FIGS. 1 and 2, heart 10 includes the upper heart chambers, the right atrium (RA) and left atrium (LA), and the lower heart chambers, the right ventricle (RV), and the left ventricle (LV). The coronary sinus (CS) is also depicted schematically in FIG. 2 extending from the opening 42 in the RA and extending laterally around the atria as the great vein 44 and into the anterior interventricular vein 46 descending inferiorly alongside the RV.

The IMD 16 (depicted partially) is implanted subcutaneously, i.e., below the skin, and includes electronic components and a power supply enclosed with a housing 26 and a connector block 27 having bores for receiving the proximal connector end assembly of the right heart cardiac leads 10 and the CS cardiac lead 100. These figures illustrate some of the possible cardiac implantation sites and routes of introduction of cardiac electrodes on cardiac leads 10 and 100 to the cardiac implantation sites in accordance with the method and apparatus of the present invention. It will be understood that the illustrated cardiac leads 10 and 100 may be used in combination in the heart 14 and/or more than one cardiac lead 10 may be employed. The cardiac leads 10 and 100 of FIGS. 1 and 2 depict possible cardiac implantation sites for single and dual chamber cardiac stimulation and/or sensing depending on the nature of the IMD 16. The illustrated cardiac leads 10 and 100 can be unipolar, bipolar or multi-polar leads and can be fabricated with pace/sense and/or cardioversion/defibrillation electrodes. Alternatively, the cardiac leads can simply bear EGM sensing electrodes and/or physiologic sensors. The present invention is related to introduction arrangement and methods for introducing a cardiac electrode and/or physiologic sensor to one of the illustrated sites and other suitable cardiac implantation sites.

In this regard, the right heart cardiac lead 10 is shown in FIG. 1 extending through the superior vena cava (SVC) 22 inferiorly through the RA and RV and lodging a distal electrode and fixation mechanism into the apex 24 of the heart 14. The lead 10 can include a passive fixation mechanism, e.g., a plurality of soft, pliant tines for engaging in interstices of the trabeculae of the RA and RV and holding a distal cardiac electrode 34 against the endocardium 15. Alternatively, and as shown in detail hereafter, the fixation mechanism and the distal cardiac electrode 34 can be combined in a distally extending helix 17 that is adapted to be screwed into the myocardium and provides active fixation therewith in the manner described in the above-incorporated, commonly assigned, '014 patent from which FIG. 1 is taken. The active fixation helix 17 is typically shrouded in a wide variety of manners during introduction through the vasculature to the cardiac implantation site to prevent the sharpened tip of the helix 17 from snagging or penetrating blood vessels. For example, the helix 17 can be covered with a soluble covering of the type described in U.S. Pat. Nos. 5,531,783 and 4,876,109, incorporated herein by reference. Once soluble coating dissolves in blood over a time period that allows the lead distal end to be advanced to a cardiac implantation site. After dissolution is complete, the exposed helical turns of helix 17 are screwed into the myocardium at cardiac implantation sites where the myocardium is thick enough to avoid penetration of the helix 17 entirely through the septum or heart chamber wall.

FIG. 1 illustrates that the helix 17 can also be affixed to other implantation sites 19 and 18 in the septum between the RV and LV chambers or that it can be attached to relatively thicker areas of the RA, e.g., the exterior atrial wall site 20 through use of the introduction arrangement and method of the present invention. It will also be understood that the helix 17 can also simply attach the distal end of the cardiac lead 10 to the depicted implantation sites 18, 19, 20 and 24 of the RV and RA and a separate cardiac electrode 34 can be provided.

FIG. 2 illustrates the introduction of a straight CS unipolar or bipolar or multi-polar cardiac lead 100 through the SVC and RA chamber and the ostium of the CS to extend alongside the LA chamber and the LV chamber. The CS cardiac lead 100 is formed with an in-line connector end assembly fitting into a bore of IMD connector block 27 in a conventional manner to couple one or more electrically insulated conductors within the lead body with one or more distal CS cardiac electrode 134. The distal CS electrode(s) 134 can be located as depicted deep within the anterior interventricular vein 46 at LV implantation site 38 adjacent to the LV for LV stimulation and/or sensing applications. For LA stimulation and/or sensing applications, the distal CS electrode(s) can be located in the great vein 47 at an implantation site 48 adjacent to the LA. The CS electrode(s) 117 are typically ring shaped and are located proximally to a distal tapered lead extension 120. The LA and LV CS leads typically do not have any distal fixation mechanism and instead rely upon the close confinement and lead body column strength to counter the relatively slow blood flow in the CS and great vein, respectively, and to maintain their cardiac electrode(s) at the cardiac implantation site(s) in the cardiac veins.

Figure 3:
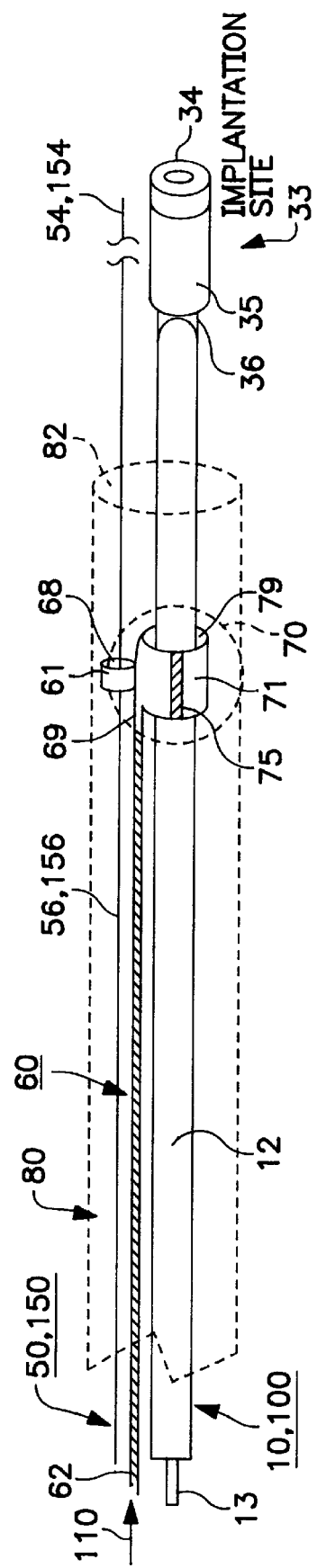
FIG. 3 is a schematic view of a distal portion of the introduction arrangement of a first embodiment of the invention employing a lead pusher for advancing an endocardial cardiac lead over a guidewire first advanced to the implantation site in a heart chamber or cardiac blood vessel illustrated in FIGS. 1 and 2.

Typically, cardiac leads 10 and 100 are implanted in the prior art employing stiffening stylets or introducer catheters or other tools as described in detail above. FIG. 3 is a plan view of the introduction arrangement of a first embodiment of the invention for introducing an endocardial cardiac lead 10 of the type illustrated in FIG. 1 into a right heart chamber and for attaching a fixation mechanism (e.g. helix 17 of FIG. 1) of the lead 10 to the myocardium or endocardium at one of the implantation sites 18, 19, 20, 24, etc., using the lead pusher 60. The arrangement of the lead pusher 60 and lead body facilitates the introduction and advancement of the endocardial cardiac lead 10 transvenously through an incision in the skin and within a patient's body to position the cardiac electrode at the cardiac implantation site.

In FIG. 3, a generic endocardial cardiac lead 10, 100 is depicted in relation to the lead pusher 60 and guiding means 50 of the first embodiment of the invention wherein the lead pusher 60 includes a combined guide body tracking and cardiac lead engaging means 70. The guiding means 50 can be a simple guidewire of any known type or a more sophisticated guidewire having a steerable distal tip, for example, or it may constitute the specific micro-catheter 150 described in detail below as long as it can be advanced through the vasculature and the heart chambers and cardiac blood vessels to one of the cardiac implantation sites described above and depicted in FIGS. 1 and 2.

The cardiac lead 10, 100 schematically shown in FIG. 3 is intended to represent any of the known types of endocardial cardiac leads adapted to be placed in any of the heart chambers and cardiac blood vessels to locate its electrode(s) 34 (or helix 17 or ring electrode 134) at one of the cardiac implantation sites described above and depicted in FIGS. 1 and 2. The cardiac lead 10 is constructed with a lead body 12, 112 having a constant lead body diameter extending between a conventional proximal lead connector end assembly (assembly 32 shown in FIGS. 10–12) and a lead distal end 33. Preferably, the arrangement of the present invention is used to advance a cardiac lead 10, 100 having a lead body 12, 112 that is highly flexible or limp and does not have a lumen extending through its length to receive a stiffening stylet. Thus, such a cardiac lead 10, 100 has insufficient column strength or torque transfer capability in its lead body 12, 112 to allow it to be advanced through the vasculature to the cardiac implantation sites depicted in FIGS. 1 and 2. A lead conductor 13, e.g., a stranded wire conductor, is electrically insulated by the lead body 12, 112 and extends between the proximal connector end assembly 32 and the lead distal end 33 where it is electrically connected with the cardiac electrode 34. The lead bodies 12 and 112 preferably have outer diameters in the range of 0.040 inches to 0.065 inches (1.0–1.65 mm).

In this illustration of the first embodiment, the distal end of the lead conductor 13 is electrically connected with a distal cardiac electrode 34 at or near the distal end of an enlarged crimping zone 35. An annular shoulder 36, is created at the proximal junction of the crimping zone 35 with the lead body 12, 112 by the enlargement crimping zone diameter that functions as a feature engaged by cardiac lead engaging means. It will be understood that the lead 10, 100 may or may not have an active or passive fixation mechanism in the lead distal end 33 which can also function as the feature engaged by the cardiac lead engaging means. Of course, the lead 10, 100 can include more than one lead conductor 13 and cardiac electrode 34 and can also include or substitute physiologic sensors with or for the cardiac electrode(s).

The combined guide body tracking and cardiac lead engaging means 70 is coupled with the lead distal end 33 and receives and slidingly engages guide body 56 of the guiding means 50 to allow the cardiac lead 10, 100 to be advanced along the guiding means 50 until the cardiac electrode 34, 134 is positioned at the cardiac implantation site. The lead pusher 60 is formed of an elongated pusher body 62 of flexible material that extends between a pusher body proximal end (e.g., pusher handle 58 shown in FIGS. 10–12) and a pusher body distal end 69 that is coupled with the guide body tracking and cardiac lead engaging means 70. The pusher body 62 has sufficient column strength to be advanced along the predetermined transvenous path to one of the cardiac implantation sites depicted in FIGS. 1 and 2 over the elongated guiding means 50 with the cardiac lead engaging means engaging the cardiac lead body 12, 112 and pulling cardiac lead 10, 100 along with it and alongside the guiding means 50.

Guide body tracking and cardiac lead engaging means 70 is formed or a cardiac lead engaging means 71 for engaging the cardiac lead body 12, 112 at or adjacent the lead distal end 33 and a guide body tracking means 61 that engages and slides over the guiding means 50. In a variation of the first embodiment, the guide body tracking means 61 loosely engages the guiding means 50 and the cardiac lead engaging means 71 loosely encircles the lead body 12, 112 and bears against the shoulder 36 of the lead body 12, 112 adjacent the lead distal end 33 to advance cardiac lead 10 distally with advancement of the pusher body 62. In this variation, the guide body tracking means 61 and the cardiac lead engaging means 71 can comprise loops or cylinders attached side by side to the pusher body distal end 69 that have a guide body tracking lumen 68 and a lead body receiving lumen 79, respectively, that are larger in diameter than the outer diameters of the guiding means 50 and lead body 12, 112, respectively. However, the diameter of the lead body receiving lumen 79 is smaller than the diameter of the shoulder 36 so that advancement force transmitted down the length of the pusher body 62 is transmitted to the lead distal end 33 to move it along the guiding means 50. An expandable opening or lead breech 75 can be provided in the loop or cylinder of the cardiac lead engaging means 71 to be opened to the diameter of the lead body 12, 112 to allow it to be inserted into or withdrawn from lead body receiving lumen 79 and closed to retain lead body 12, 112 within it. The constant diameter guide body 56 of the guiding means 50 can be freely inserted into or withdrawn from the guide body tracking lumen 68.

FIG. 3 also shows that an introducer catheter 80 can also be employed having an introducer lumen 82 sized to receive the arrangement of the lead 10, 100, guiding means 50 and lead pusher 60. Such an introducer catheter 80 can be employed particularly to introduce the arrangement through the skin incision and the incision in the vein, and may be advanced further through the vasculature to make it easier to traverse bends and narrowed sections thereof. The introducer catheter 80 can also be advanced along the predetermined transvenous path within the vasculature to position the introducer lumen distal end opening in relation to a cardiac implantation site.

Thus, when the arrangement is assembled as shown in FIG. 3, the cardiac lead 10, 100 can be advanced through the vasculature to the cardiac implantation sites depicted in FIGS. 1 and 2 by advancement of the proximal end of the pusher body 62 in the direction of the arrow 110. When the pusher body 62 is withdrawn proximally, the guide body tracking means 61 is retracted proximally over the guide body 56, and the cardiac lead engaging means 71 is retracted proximally over the lead body 12, 112 until they both are withdrawn from the incision in the exposed vein and the skin incision, where the arrangement can be disassembled.

Figure 6:
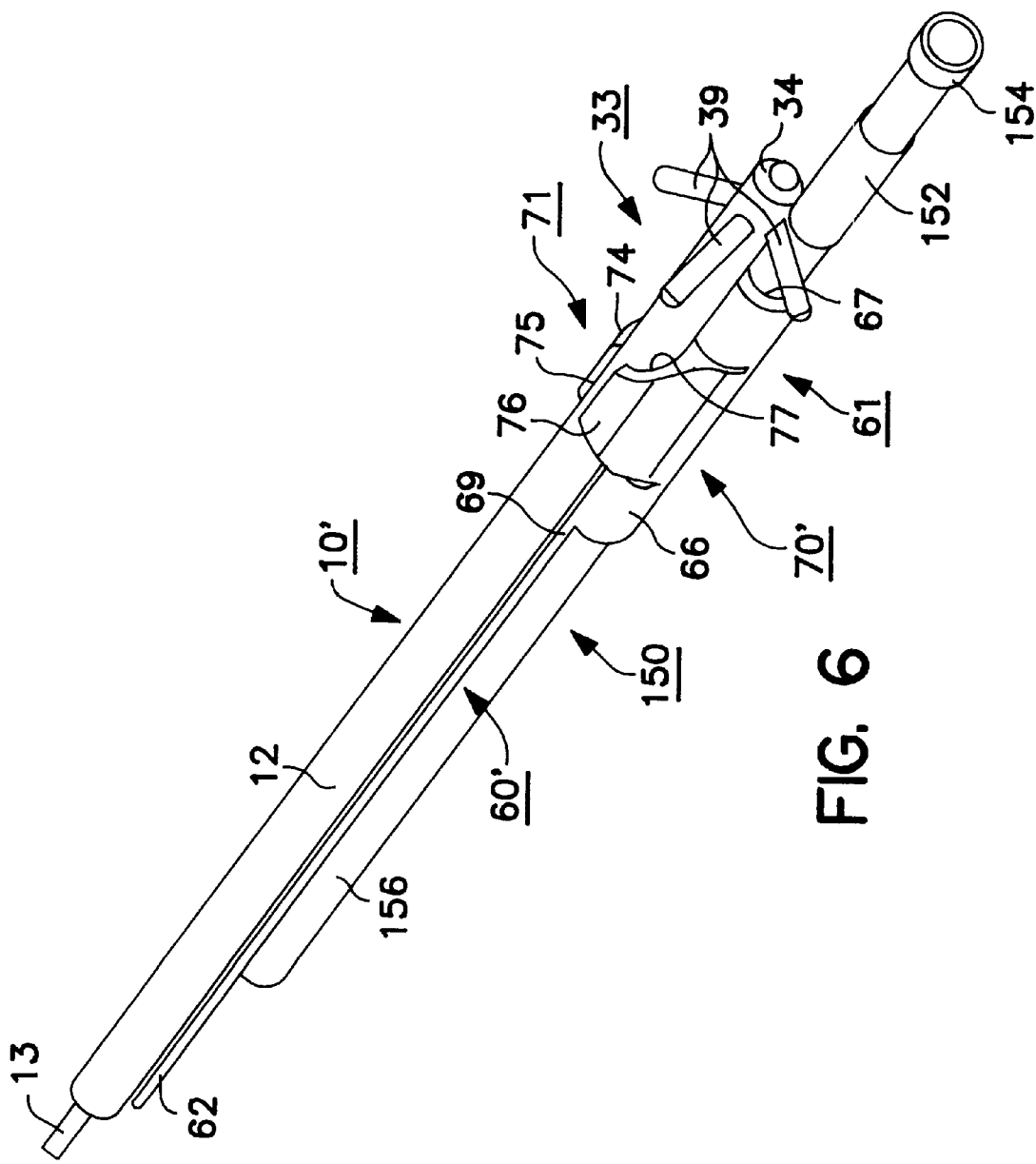
FIG. 6 is a partial perspective view of an introduction arrangement employing the combined guide body tracking and cardiac lead engaging means of FIG. 5 for selectively gripping the lead body of an endocardial tined lead during advancement over the guide body to the cardiac implantation sites of FIG. 1 and a release mechanism usable therewith.

It should be noted that any of the cardiac leads 10', 10" and 100 illustrated in FIGS. 6–8 and described hereafter can be employed in the arrangement of this variation of the first embodiment of the invention if provided with a shoulder 36 or other feature to engage the cardiac lead engaging means 71. The plurality of soft pliant tines 39 of the endocardial tined lead 10' illustrated in FIG. 6 can function as the feature engaged by the cardiac lead engaging means 71.

Figure 4:
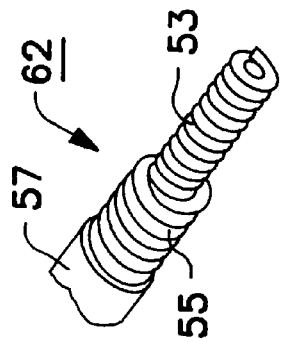
FIG. 4 is detailed view of the construction of the pusher body providing torque transmission capability and column strength for advancing the cardiac lead over the guide body to the implantation site.

The pusher body 62 is rod or wire shaped and can be a simple, solid metal, stylet wire having a relatively small outer diameter or can be of more complex construction. FIG. 4 is a detailed view of an alternative construction of the pusher body 62 providing torque transmission capability and column strength for advancing the cardiac lead 10, 100 over the guide body 56 to the guide body distal end 54 at the cardiac implantation site. In this embodiment, the pusher body 62 and is formed of a torque cable formed of two coaxial wire coils 53 and 55 wound in opposite winding directions. The outer wire coil 55 can be left uncoated or can be coated with an elastomeric compound in a sheath 57 to control the stiffness and wetability of the pusher body 62 for ease of introduction through the transvenous path and the cardiac blood vessels.

In a further variation of the first embodiment illustrated in FIGS. 5–9, a directional balloon micro-catheter 150 is employed as the elongated guiding means 50 with a combined guide body tracking and cardiac lead engaging means 70' that provides for the selective and remote adjustment of the lead body receiving lumen 79 between a clamped state that grasps the lead body and a released state that releases the lead body 12 or 112. In the clamped state, the diameter of the lead body receiving lumen 79 is sized to tightly grasp the lead body 12, 112 adjacent to the distal lead end. In the released state, the diameter of the lead body receiving lumen 79 is expanded, allowing the lead body receiving cylinder to be advanced or retracted over the lead body 12, 112 or allowing the lead body to pass through the lead breach 75. The tight grasp in the clamped state allows the application of rotational torque to the lead body 12, 112 through rotation of the arrangement at the proximal ends of the pusher body 62, the cardiac lead 10, 100 and the micro-catheter 150 extending outside the incision in the patient's skin.

Figure 5:
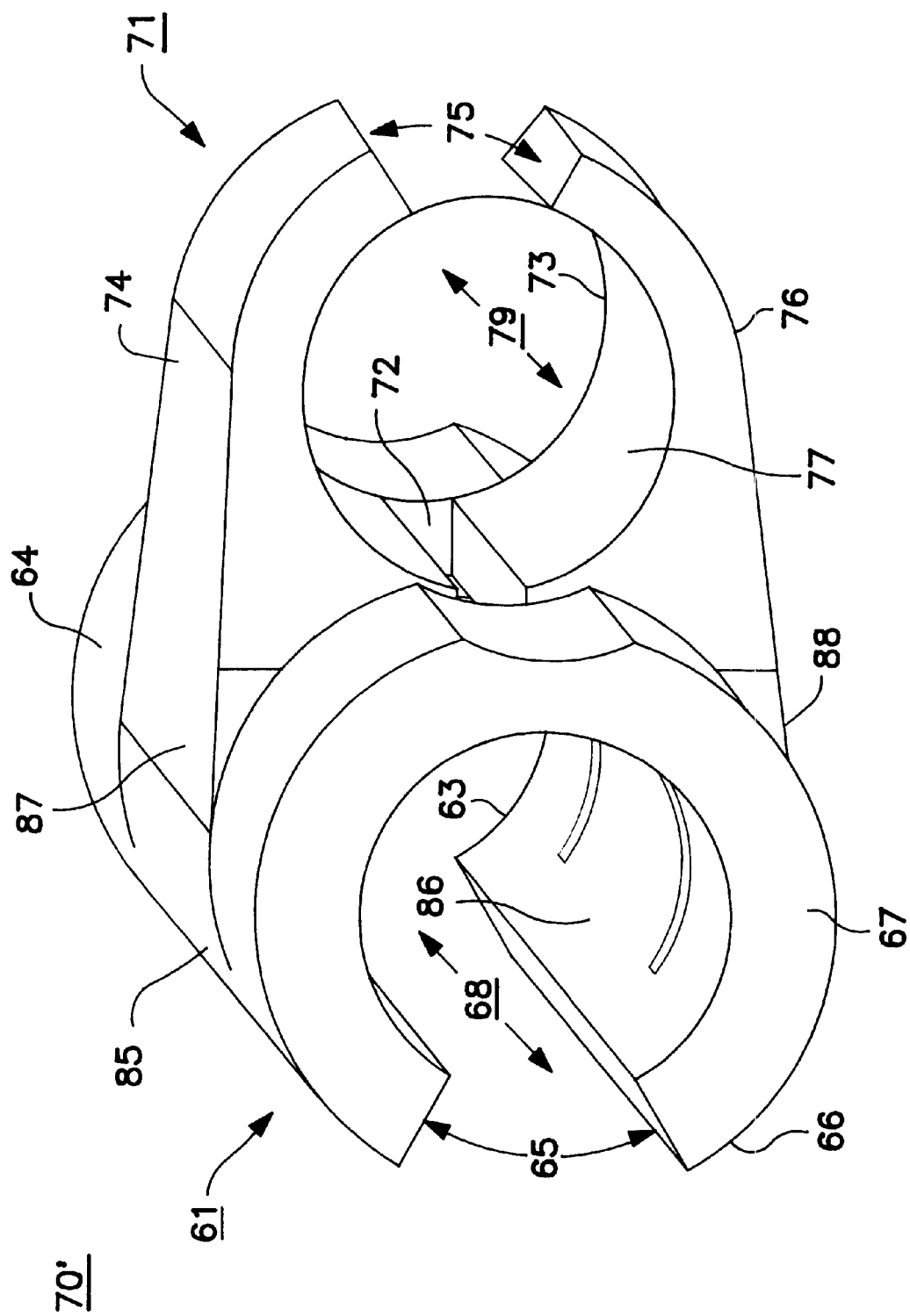
FIG. 5 is an expanded perspective view of a combined guide body tracking and cardiac lead engaging means attached to the pusher body of the lead pusher of FIGS. 6–8 having a clamped state and a released state for selectively gripping and releasing the lead body.

FIG. 5 is an expanded perspective view of a combined guide body tracking and cardiac lead engaging means 70' attached to the pusher body 62 shown in FIGS. 6–8 having a clamped state and a released state for selectively gripping and releasing the lead body 12, 112 in the lead body receiving lumen 79. In this variation of the first embodiment, the guide body tracking means 61 and the cardiac lead engaging means 71 are molded as a single piece from plastic in the form of cylinders that are joined together in side by side relation and attached at the junction to the pusher body distal end 69. The guide body tracking means 61 and the cardiac lead engaging means 71 define a guide body tracking lumen 68 and a lead body receiving lumen 79, respectively. The guide body tracking lumen 68 extends between proximal and distal guide body tracking lumen end openings 63 and 67, and the lead body receiving lumen 79 extends between proximal and distal lead body receiving lumen end openings 73 and 77.

The cylindrical guide body tracking means 61 is formed of proximal and distal C-shaped elements 64 and 66 that are joined together along either side of an elongated guide body breech 65 by axially extending bridge members 85 and 86 extending between the proximal and distal guide body tracking lumen end openings 63 and 67. The generally cylindrical lead engaging means 71 is formed of two half cylinder walls 74 and 76 that are separated from one another by an elongated lead breech 75 extending between the proximal and distal guide body tracking lumen end openings 73 and 77. The other ends of the half cylinder walls 74 and 76 are separated from one another by a gap 72 and are also separated from the sides of the proximal and distal C-shaped elements 64 and 66 but are attached along the axially extending bridge elements. Therefore, these ends of the half cylinder walls 74 and 76 are coupled to the axially extending bridge members through living hinges 87 and 88, respectively.

The combined guide body tracking and cardiac lead engaging means 70' is shown in the clamped state in FIGS. 5–8. The diameter of the lead body receiving lumen 79 is selected to be somewhat less than the diameter of the lead body 12, 112 to tightly grasp it in the normal, clamped state. However, the diameter of the lead body receiving lumen 79 can be expanded in a released state that releases the grasp on lead body 12, 112 and allows the cardiac lead engaging means 71 to be retracted over the cardiac lead body 12, 112. The expansion of the lead body receiving lumen diameter into the released state is effected by the selective expansion of the diameter of the guide body tracking lumen 68 which causes the side walls 74 and 76 to separate apart at the living hinges 87 and 88 and the elongated lead breech 75 to widen. The expansion of the guide body tracking lumen 68 is effected by locating an expandable balloon 152 on the exterior surface of the micro-catheter 150 within the guide body tracking lumen 68 and expanding the balloon to separate the side walls 64 and 66 and to separate the gap 72. The separation of the gap 72 is effected through outward bending of the living hinges 87 and 88 that in turn causes the side walls 74 and 76 to separate apart, thereby widening the breech 75 and expanding the lead body receiving lumen 79.

FIGS. 6–8 are perspective views of distal end portions of the arrangement of this variation of the first embodiment of the invention for implanting various types of cardiac leads 10 and 100. In these views, the micro-catheter 150 is formed in the manner of a balloon catheter having an expandable balloon 152 located proximal to the enlarged diameter, micro-catheter distal end 154. A proximal handle and balloon dilation assembly (assembly 151 of FIGS. 10–12) is coupled to the proximal end of the guide body 156. A balloon inflation lumen extends within guide body 156 between the proximal handle and balloon dilation assembly 151 and the distal balloon 152. If the micro-catheter 150 cannot be advanced through the vasculature and to the cardiac implantation site without assistance, it can include a guidewire lumen extending between its proximal and distal ends so that it can be advanced over a guidewire already advanced to the cardiac implantation site. Such micro-catheters include the Model WP, DWP and SafPace™ WPIP pressure measurement catheters available in 4 French—8 French body diameters from B. Braun Medical Inc., located in Bethlehem, Pa.. Alternatively, the micro-catheter 150 can be of the type having a steerable distal end 154 that is deflectable by manipulation at its proximal end of steering wires extending through steering wire lumens extending between its proximal and distal ends as described in commonly assigned U.S. Pat. No. 5,545,200, incorporated herein by reference.

FIG. 6 is a partial perspective view of an introduction arrangement employing the combined guide body tracking and cardiac lead engaging means 70' of FIG. 5 for selectively gripping the lead body 12 of an endocardial tined lead 10' during advancement over the micro-catheter 150 to the cardiac implantation sites of FIG. 1. The endocardial tined lead 10' is formed with a plurality of the soft pliant tines 39 extending rearwardly from the distal tip electrode 34 in a conventional manner for passive fixation, cardiac leads of this type. The distal tip electrode 34 is urged against the endocardium as the tines 39 are lodged in interstitial spaces of the trabeculae at certain cardiac implantation sites in the RA and RV shown in FIG. 1. The arrangement of the present invention facilitates that positioning of the distal tip electrode 34.

FIG. 7 is a partial perspective view of an introduction arrangement employing the combined guide body tracking and cardiac lead engaging means 70' of FIG. 5 for selectively gripping the lead body 12 of an endocardial screw-in lead 10" during advancement over the micro-catheter 150 to the cardiac implantation sites of FIG. 1. The helix 17 extending distally from the lead distal end 33 to a sharpened tip provides the function of a cardiac electrode and an active fixation mechanism. The active fixation helix 17 is typically shrouded in a wide variety of manners during introduction through the vasculature to the cardiac implantation site to prevent the sharpened tip of the helix 17 from snagging or penetrating blood vessels. As illustrated in FIG. 7, the helix 17 is covered with a soluble covering 37 of the type described in the above-incorporated '783 and '109 patents which dissolves in blood over a time period that allows the lead distal end to be advanced to a cardiac implantation site. After dissolution is complete, the exposed helical turns of helix 17 are screwed into the myocardium at cardiac implantation sites where the myocardium is thick enough to avoid penetration of the helix 17 entirely through the septum or heart chamber wall.

FIG. 8 is a partial perspective view of an introduction arrangement employing the combined guide body tracking and cardiac lead engaging means 70' of FIG. 5 for selectively gripping the lead body 112 of an endocardial CS lead 100 during advancement over the micro-catheter 150 to the cardiac implantation sites of FIG. 2. The CS lead 100 includes the CS ring electrode 134 on the lead distal end 133 and the tapered lead extension 120 extending distally therefrom.

Figure 9:
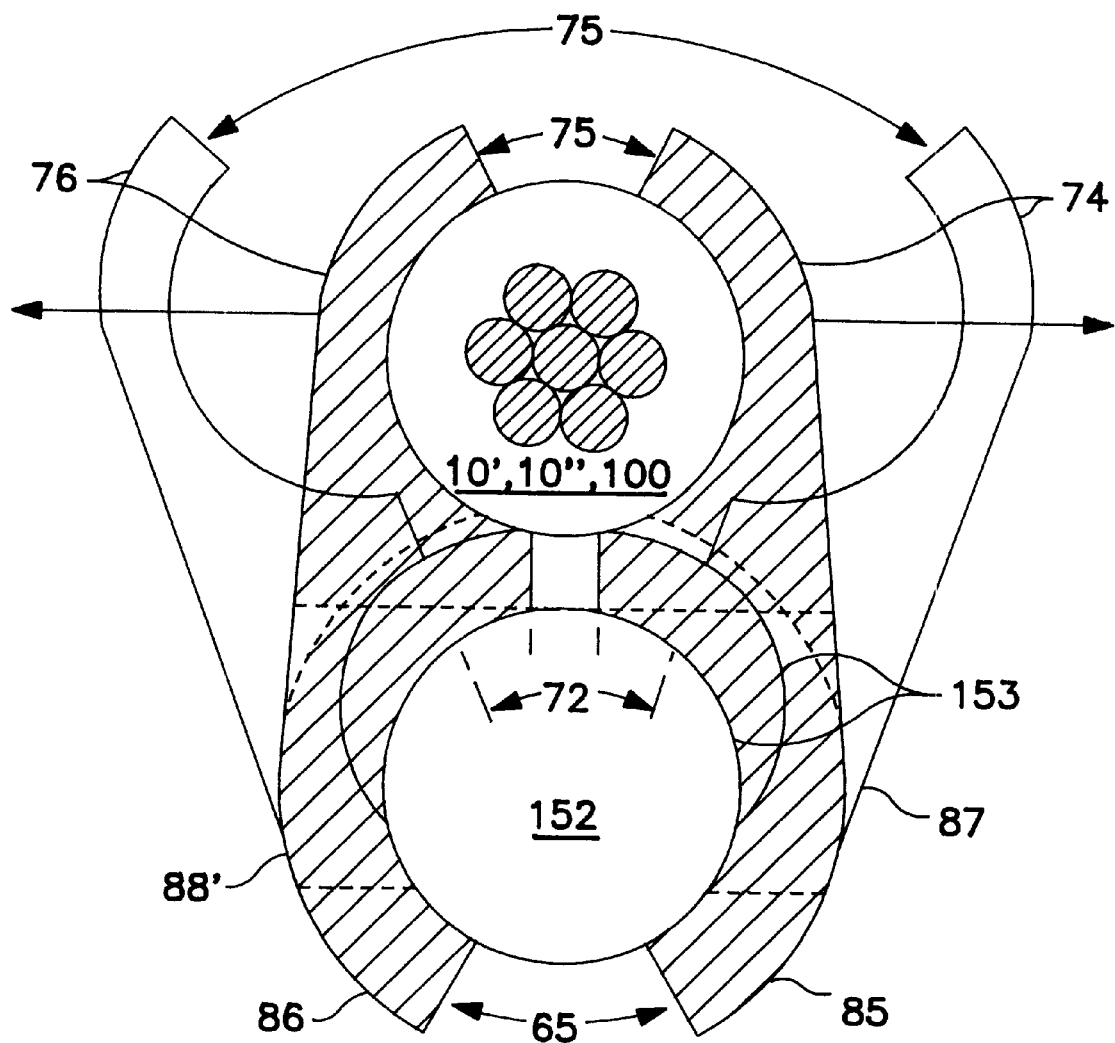
FIG. 9 is a view of the use of a balloon on a micro-catheter of FIGS. 6–8 to place the cardiac lead engaging means in the released state to release the lead body in preparation for withdrawal of the lead pusher over the guide body.

It should be noted that the diameter of the guide body tracking lumen 68 normally exceeds the outer diameter of the guide body 156 and the un-inflated expandable balloon 152. It will be understood that the expandable balloon 152 is received in the guide body tracking lumen 68 by advancement of the pusher body 62 until the distal edge of the cylindrical guide body tracking means 61 abuts the enlarged diameter, micro-catheter distal end 154. FIG. 9 shows this relative positioning of balloon 152 within guide body tracking lumen 68 in faint, cross-hatched lines. The expansion of the balloon side wall 153 shown in solid lines forces it into and widens the gap 72 as the living hinges 87 and 88 bend outward from their attachment with the bridge elements 85 and 86. As the balloon 152 expands and forces into the gap 72, its force causes the side walls 74 and 76 to separate apart, thereby widening the breech 75 and expanding the lead body receiving lumen 79 all as shown in solid lines. This allows the cardiac lead 10', 10", 100 to be released laterally through the widened breech 75.

Figure 10:
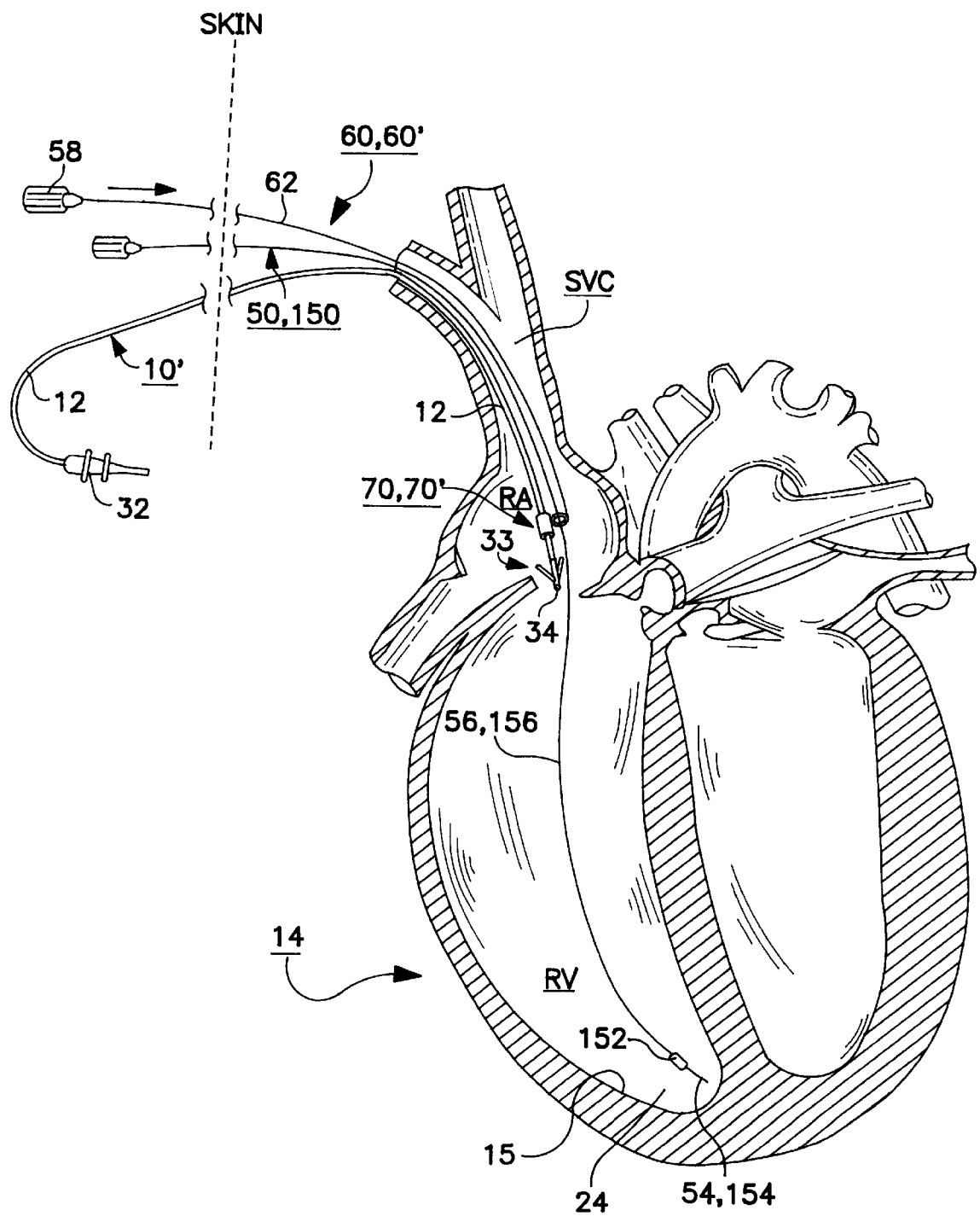
FIGS. 10–12 illustrate steps in the advancement of a cardiac lead to an implantation site employing the arrangement of the first embodiment of the invention.
Figure 11:
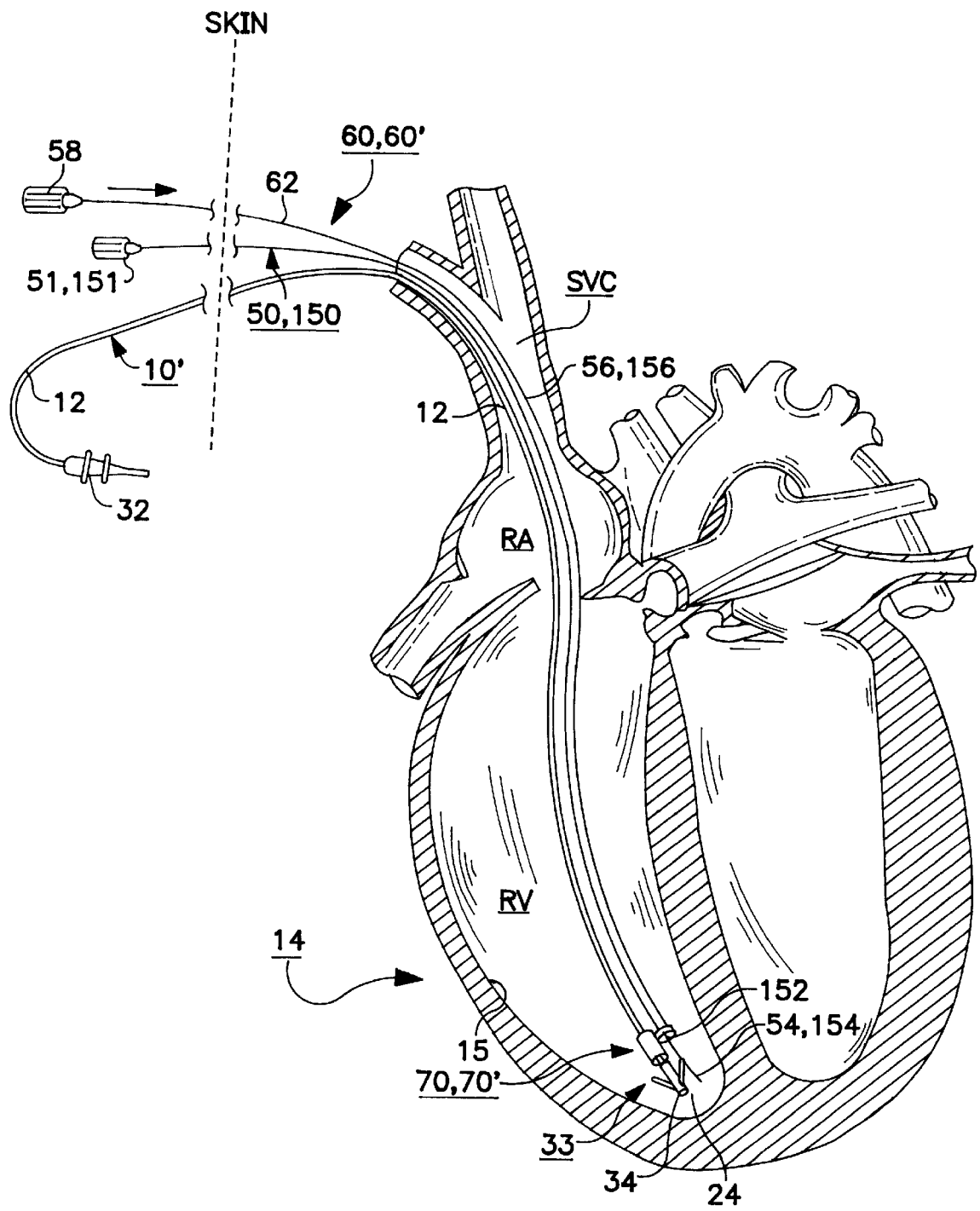
Figure 12:
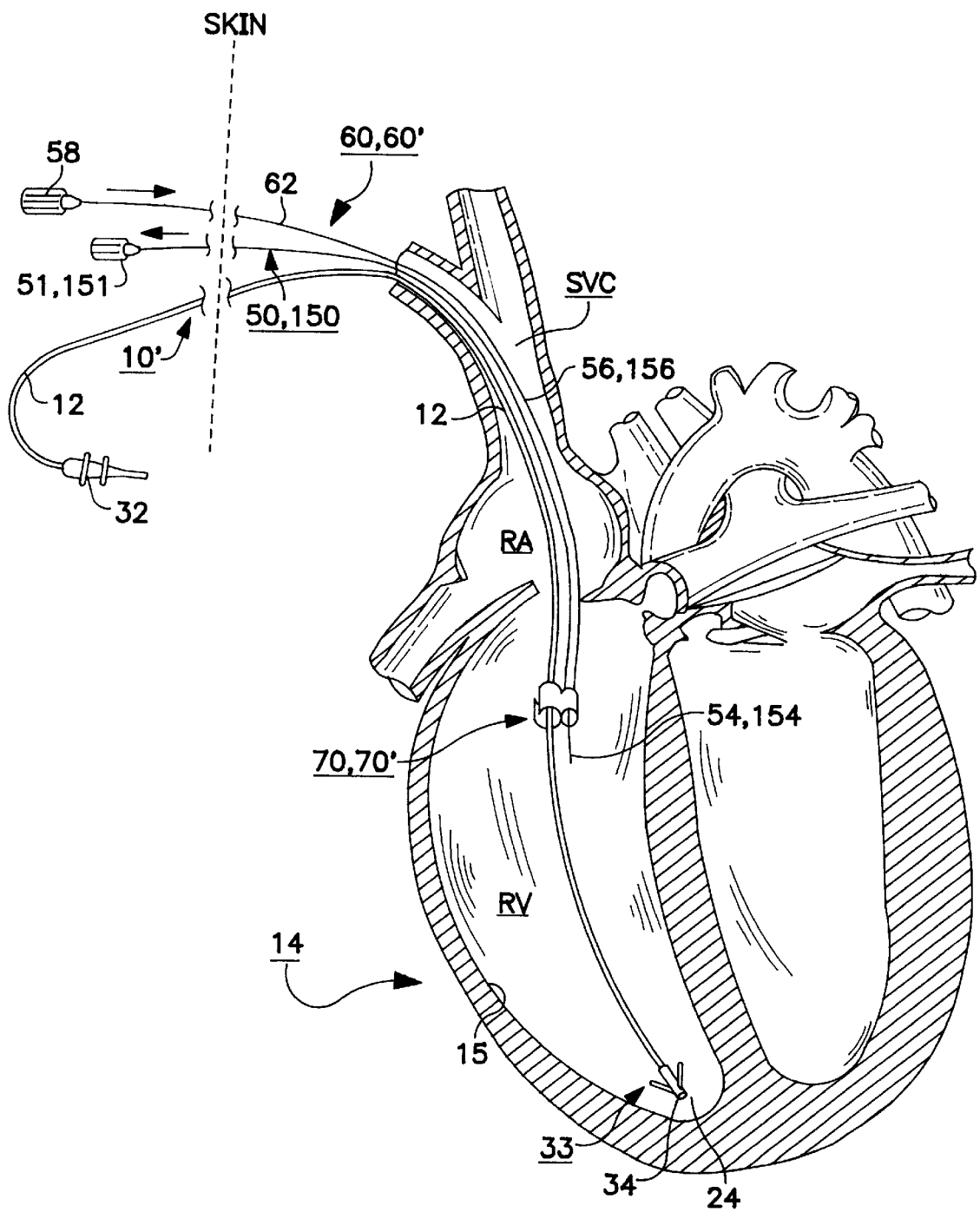
Figure 13:
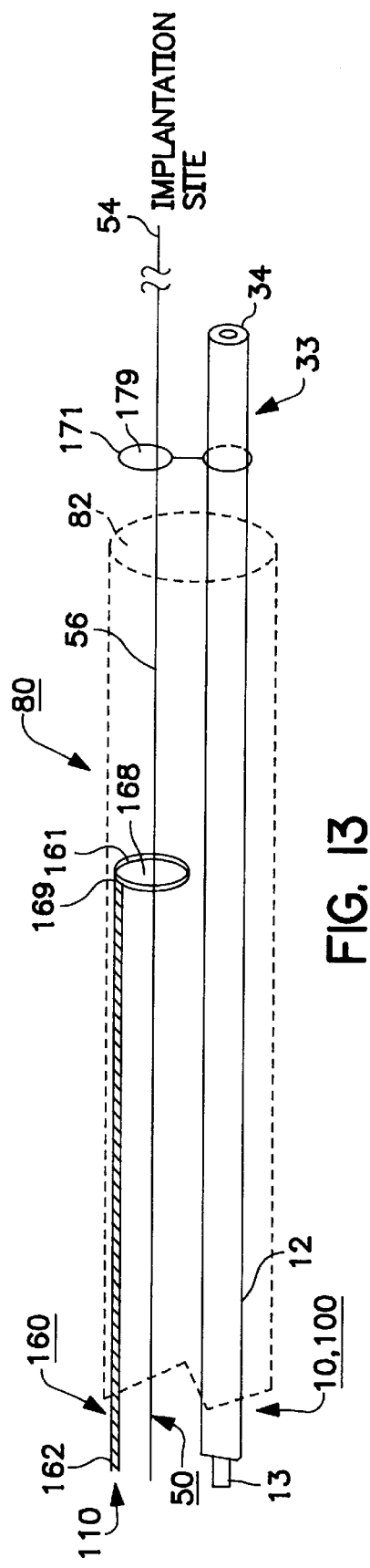
FIG. 13 is a schematic view of a distal portion of the introduction arrangement of a first embodiment of the invention employing a lead pusher and a resorbable loop attached to the lead distal end for advancing the endocardial cardiac lead over a guidewire first advanced to the implantation site in a heart chamber or cardiac blood vessel illustrated in FIGS. 1 and 2.

FIGS. 10–12 illustrate steps in the advancement of a tined cardiac lead 10' to an exemplary implantation site 24 in the RV employing the arrangement of the variations of the first embodiment of the invention described above. In FIG. 10, the arrangement of the tined lead 10', the guiding means 50 or 150 and the lead pusher 60 or 60' is assembled as shown in FIGS. 3 or 6 advanced through the incision in the patient's skin and an incision in a suitable vein. After the assembly is formed, the guide body distal end 54 is first advanced through the predetermined path in the vasculature, the SVC 22, the RA and into the trabeculae at the apex 24 of the RV as shown in FIG. 10. Then the endocardial tined lead 10' is pushed along the predetermined path as the proximal handle 58 of the lead pusher 60 or 60' is advanced to advance the combined guide body tracking and cardiac lead engaging means 70 or 70' over the guiding means 50 or 150. The advancement into the SVC is also depicted in FIG. 10.

FIG. 11 depicts how the lead distal end 33 and distal electrode 34 of the tined lead 10' are lodged in the apex 24 of the RV. At this juncture, the guiding means 50 and lead pusher 60 of the of the first variation of the first embodiment of the invention depicted in FIG. 3 are simply withdrawn or retracted back out through the same predetermined path until they are withdrawn through the incision in the skin and disassembled from the lead body 12. In accordance with the second variation of the first embodiment, the balloon 152 on the micro-catheter 150 is located within the guide body tracking lumen and inflated to increase the lead body receiving lumen of the combined guide body tracking and cardiac lead engaging means 70' as described above to release the lead body 12.

FIG. 12 depicts the partial withdrawal of the guiding means 50 or 150 and the lead pusher 60 or 60'. The lead body either is preferably released laterally through the lead breach so that the balloon 152 can then be deflated to ease withdrawal through the vasculature and incisions. Alternatively, the lead body can be loosely retained within the lead body receiving lumen in the released state and the assembly of the inflated balloon and the guide body tracking means and the lead engaging means can be withdrawn distally over the lead body through the vasculature and incisions and released from the lead body outside the patient's body. In this variation of the first embodiment, the balloon 152 on the micro-catheter 150 remains inflated throughout the withdrawal process to maintain the increased diameter of the lead body receiving lumen of the combined guide body tracking and cardiac lead engaging means 70'.

FIGS. 13–17 depict a second embodiment of the arrangement of the present invention for introducing any of the leads 10, 10', 10" or 100 or other endocardial cardiac leads wherein the cardiac lead engaging means is part of or coupled with a distal portion of the lead body 12 and advanced by a lead pusher 160. In this embodiment, the simple guiding means 50, i.e., a guidewire, can be used to advantage, and consequently, this embodiment will be described hereafter assuming such use. But, it will be understood that the arrangement and method of this embodiment can also be used employing a more complex guidewire or micro-catheter 150 described above.

In this embodiment, the cardiac lead engaging means comprises a feature, e.g. a lead engaging loop 171, formed at the lead distal end 33 having a guide body engaging lumen 179 for receiving and slidingly engaging the guide body 56 to allow the lead distal end 33 to be advanced distally over the guide body 56. In this case, the guide body tracking means 161 is a guide body tracking loop or cylinder attached to the pusher body distal end 169 of lead pusher 160 that fits over the guide body 156 and can be advanced distally or retracted proximally by manipulation of the proximal end of pusher body 162 outside the incision in the patient's skin. During advancement, the guide body tracking loop 161 engages the lead engaging loop 171 and slidingly advances the lead distal end 33 distally along the guide body 156 upon advancement of the pusher body 162 to thereby allow the cardiac lead 10, 100 to be advanced alongside the guide body 56 until the cardiac electrode 34 is positioned at the cardiac implantation site. Then, the guide body 56 and pusher body 162 including the guide body tracking loop 161 are retracted proximally through the patient's vasculature and incisions. Preferably, the lead engaging loop 171 is formed of a flexible loop of resorbable material extending outwardly of the lead body 12 that dissolves within the patient's body within a predetermined time, e.g. a few days, following implantation.

Figure 14:
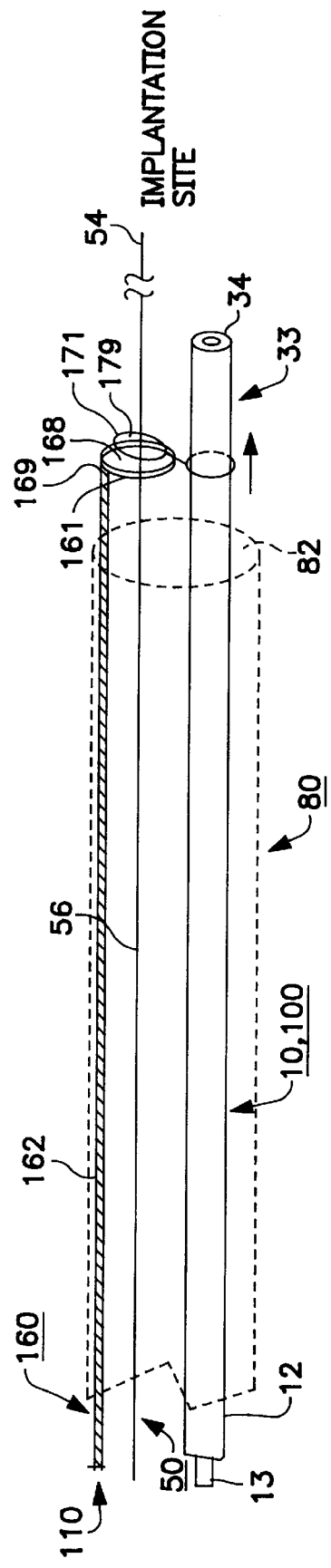
FIG. 14 is a schematic view of the engagement of the lead pusher with the resorbable loop to advance the lead over the guidewire to the implantation site in a heart chamber or cardiac blood vessel illustrated in FIGS. 1 and 2.
Figure 15:
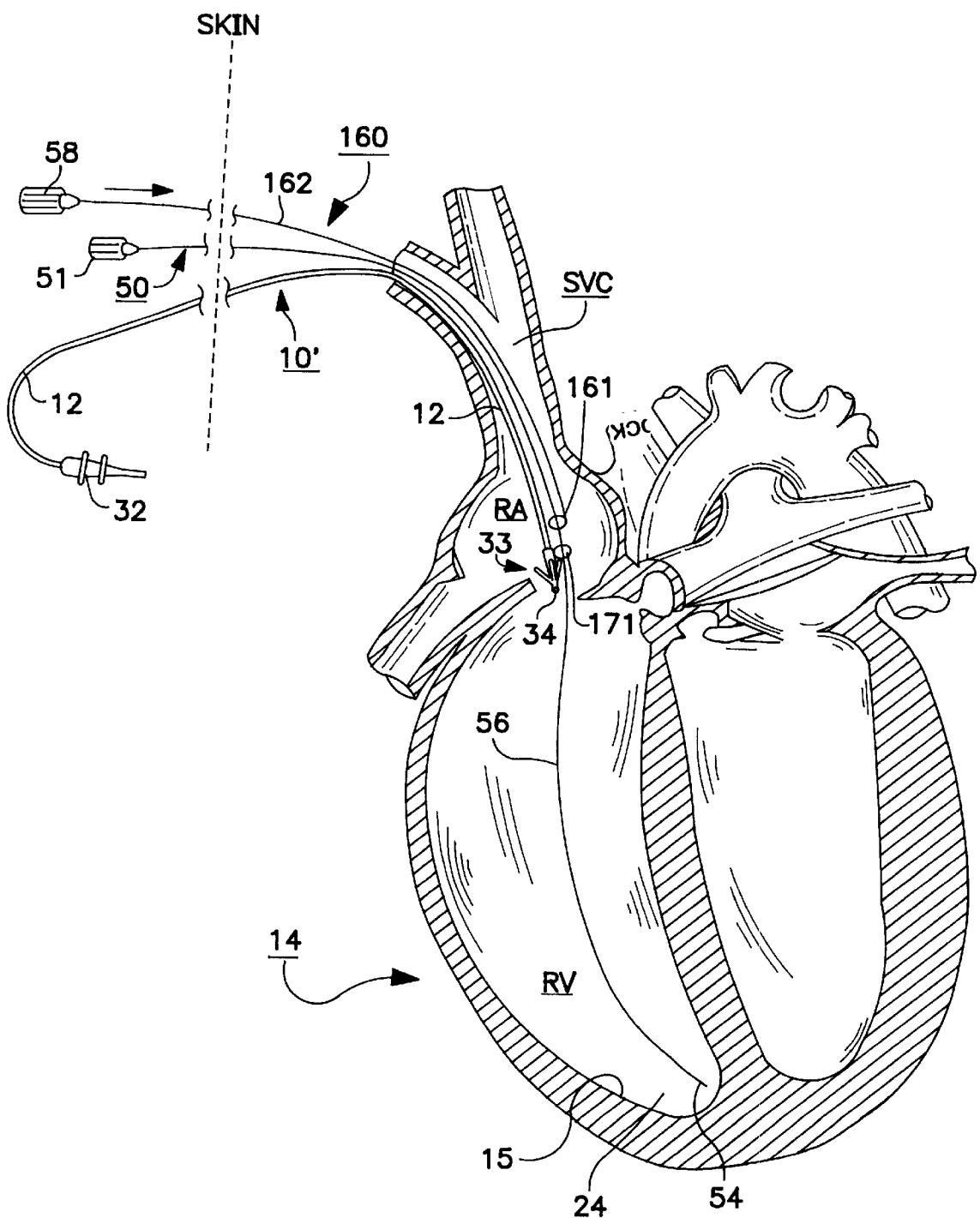
FIGS. 15–17 illustrate steps in the advancement of a cardiac lead to an implantation site employing the arrangement of the first embodiment of the invention.
Figure 16:
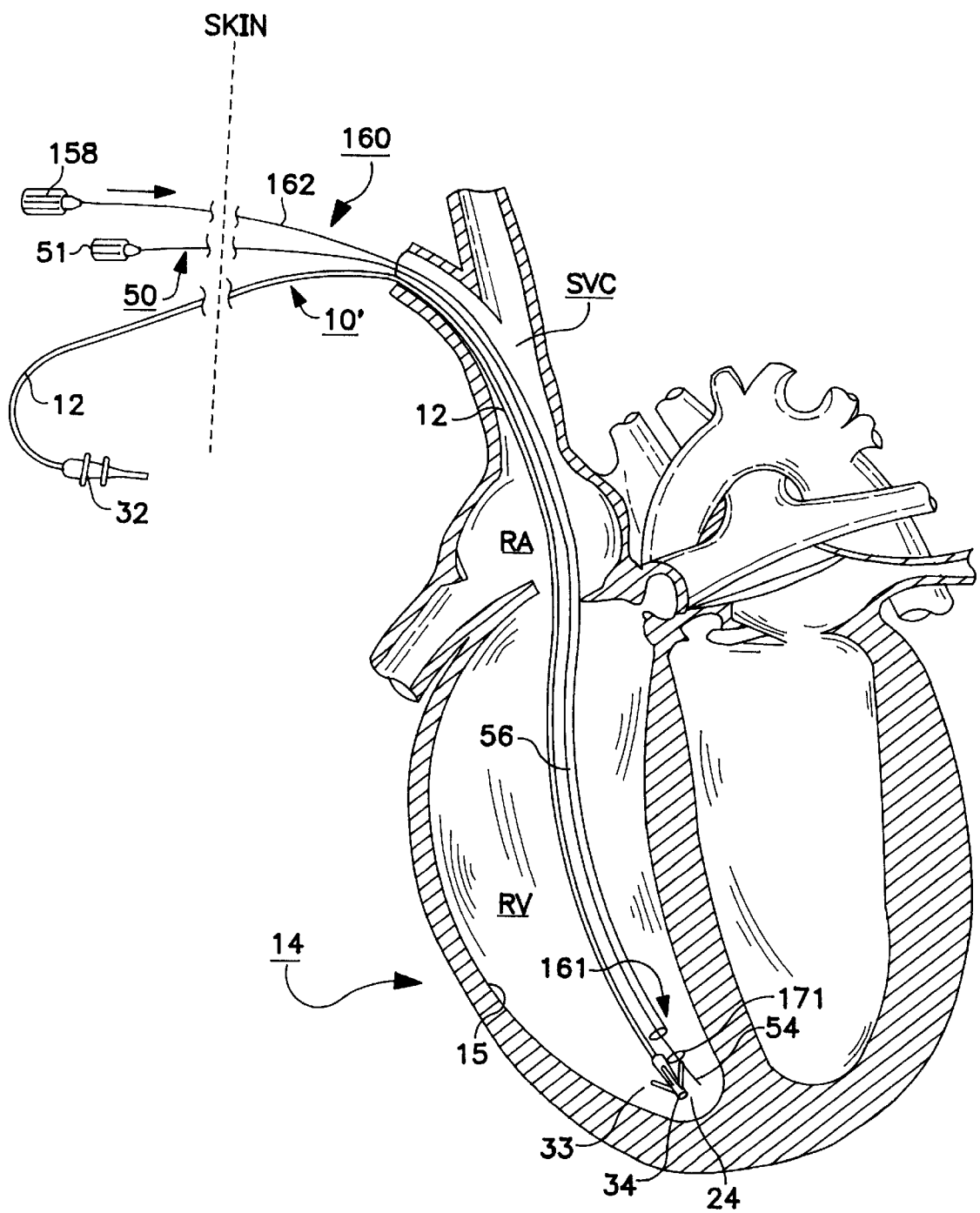
Figure 17:
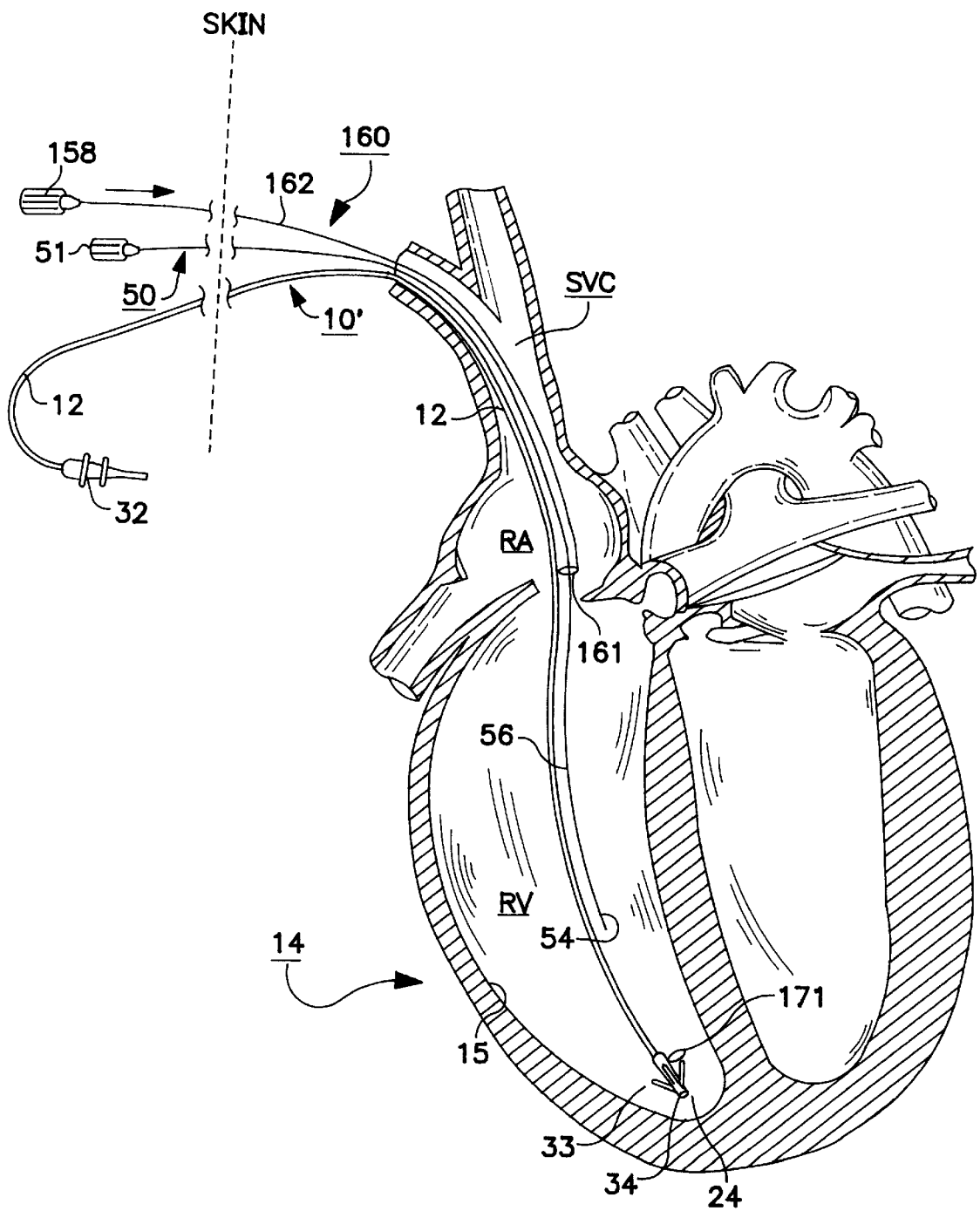

As shown in FIGS. 14–16, when the guide body tracking lumen 168 of the guide body tracking loop 161 is fitted over the guide body 56, it pushes against the lead engaging loop 171 and advances it over the guide body 56 to thereby pull the cardiac lead body alongside the guide body 56 until the cardiac electrode 34 is positioned at the cardiac implantation site. Once the cardiac electrode 34 is positioned and any fixation mechanism is deployed, the guiding means 50 and the lead pusher body 162 and guide body tracking loop 161 are simply withdrawn proximally as shown in FIG. 17. The guiding means 50 or 150 is retracted through the lead engaging loop lumen until the guide body distal end 54 passes through it, thereby releasing the cardiac lead body 12 from the guiding means 50. The lead engaging loop 171 is preferably formed of a resorbable material, e.g., a resorbable suture material, that effectively dissolves in a few days after implantation.

While particular embodiments of the invention have been disclosed herein in detail, this has been done for the purposes of illustration only, and is not intended to limit the scope of the invention as defined in the claims which follow. It is to be understood that various substitutions, alterations, or modifications can be made to the disclosed embodiment without departing from the spirit and scope of the claims. The above described implementations are simply those presently preferred or contemplated by the inventors, and are not to be taken as limiting the present invention to the disclosed embodiments. It is therefore to be understood, that within the scope of the appended claims, the invention may be practiced otherwise than as specifically described without actually departing from the spirit and scope of the present invention.

We claim:

1. An arrangement to facilitate the introduction and advancement of an endocardial cardiac lead transvenously within a patient's body to position an electrode of the cardiac lead at a cardiac implantation site, the lead including a lead body extending between a lead proximal end and a distal lead end, a lead conductor extending within said lead body between said proximal and distal lead ends, and an electrode at or adjacent said lead distal end electrically connected to said lead conductor, said arrangement comprising:

elongated guiding means for guiding the transvenous introduction and advancement of said endocardial lead to position said electrode at said cardiac implantation site and comprising an elongated flexible guide body extending between a guide body proximal end and a guide body distal end and capable of being advanced transvenously to position said guide body distal end in relation to said cardiac implantation site; and pusher means formed of an elongated pusher body of flexible material and extending between a pusher body proximal end and a pusher body distal end for advancing said cardiac lead transvenously alongside said guide body, said pusher means further comprising:

guide body tracking means coupled with said pusher body distal end for receiving and slidingly engaging said guide body as said pusher body proximal end is advanced; and cardiac lead engaging means for engaging said cardiac lead and coupled with said guide body tracking means to allow said cardiac lead to be advanced with advancement of said guide body tracking means along said guide body as said pusher body proximal end is advanced until said electrode is positioned at said cardiac implantation site, said guide body tracking means and said cardiac lead engaging means both fixedly attached to said pusher body distal end; and wherein said cardiac lead engaging means comprises means for bearing against said lead body adjacent said lead distal end to advance said cardiac lead with distal advancement of said pusher body and said cardiac lead engaging means further comprises a lead breach normally having a narrow breach width which prevents said lead body from passing therethrough and means for widening said lead breach to a wider breach width to allow said lead body to pass therethrough.

2. An arrangement to facilitate the introduction and advancement of an endocardial cardiac lead transvenously within a patient's body to position an electrode of the cardiac lead at a cardiac implantation site, the lead including a lead body extending between a lead proximal end and a distal lead end, a lead conductor extending within said lead body between said proximal and distal lead ends, and an electrode at or adjacent said lead distal end electrically connected to said lead conductor, said arrangement comprising:

elongated guiding means for guiding the transvenous introduction and advancement of said endocardial lead to position said electrode at said cardiac implantation site and comprising an elongated flexible guide body extending between a guide body proximal end and a guide body distal end and capable of being advanced transvenously to position said guide body distal end in relation to said cardiac implantation site; and pusher means formed of an elongated pusher body of flexible material and extending between a pusher body proximal end and a pusher body distal end for advancing said cardiac lead transvenously alongside said guide body, said pusher means further comprising:

guide body tracking means coupled with said pusher body distal end for receiving and slidingly engaging said guide body as said pusher body proximal end is advanced; and cardiac lead engaging means for engaging said cardiac lead and coupled with said guide body tracking means to allow said cardiac lead to be advanced with advancement of said guide body tracking means along said guide body as said pusher body proximal end is advanced until said electrode is positioned at said cardiac implantation site, said guide body tracking means and said cardiac lead engaging means both fixedly attached to said pusher body distal end; and wherein said cardiac lead engaging means comprises means for bearing against said lead body adjacent said lead distal end to advance said cardiac lead with distal advancement of said pusher body and said cardiac lead engaging means further comprises a lead breach normally having a narrow breach width sized such that said lead engaging means tightly bears against said lead body and means for widening said lead breach to a wide breach width to release said lead body to allow said lead engaging means to be withdrawn proximally along said lead body.

3. The arrangement of claims 1 or 2, wherein said guide body tracking means comprises a guide body tracking loop attached to said pusher body distal end and having a guide body tracking lumen dimensioned to receive said guide body.

4. An arrangement to facilitate the introduction and advancement of an endocardial cardiac lead transvenously within a patient's body to position an electrode of said cardiac lead at a cardiac implantation site, said lead including a lead body extending between a lead proximal end and a distal lead end, a lead conductor extending within said lead body between said proximal and distal lead ends, and an electrode at or adjacent said lead distal end electrically connected to said lead conductor, said arrangement comprising:

elongated guiding means for guiding the transvenous introduction and advancement of said endocardial lead to position said electrode at said cardiac implantation site and comprising an elongated flexible guide body extending between a guide body proximal end and a guide body distal end and capable of being advanced transvenously to position said guide body distal end in relation to said cardiac implantation site;

pusher means formed of an elongated pusher body of flexible material and extending between a pusher body proximal end and a pusher body distal end for advancing said cardiac lead transvenously alongside said guide body, said pusher means further comprising:

guide body tracking means coupled with said pusher body distal end having a guide body tracking lumen for receiving and slidingly engaging said guide body as said pusher body proximal end is advanced; and cardiac lead engaging means for clamping said cardiac lead body and coupled with said guide body tracking means to allow said cardiac lead to be advanced with advancement of said guide body tracking means along said guide body as said pusher body proximal end is advanced until said electrode is positioned at said cardiac implantation site; and means for releasing said cardiac lead from said engaging means to enable transvenous retraction of said pusher means after said cardiac lead is advanced to position said electrode at said cardiac implantation site.

5. The arrangement of claim 4 wherein:

said elongated guiding means comprises an elongated catheter having a catheter body extending between a catheter body distal end and a catheter body proximal end, an inflatable balloon at the catheter body distal end, and a balloon inflation lumen extending between the catheter body proximal end and the inflatable balloon for selectively inflating and deflating the balloon;

said cardiac lead engaging means comprises a lead body engaging cylinder enclosing a lead body receiving lumen extending between proximal and distal lead body receiving lumen end openings through which said lead body extends;

said guide body tracking means comprises a guide body tracking cylinder enclosing a guide body tracking lumen extending between proximal and distal guide body tracking lumen end openings through which said guide body extends with said balloon deflated; and said releasing means comprises means responsive to the inflation of said balloon within said guide body tracking lumen for expanding said lead body receiving lumen to release said lead body.

6. The arrangement of claim 5, wherein said cardiac lead engaging means further comprises a lead breach extending between said proximal and distal guide body tracking lumen end openings normally having a narrow breach width when said lead body is clamped to prevent said lead body from passing therethrough and wherein said releasing means comprises means for widening said lead breach to a wide breach width to allow said lead body to pass therethrough upon expansion of said balloon.

7. The arrangement of claim 5, wherein said cardiac lead engaging means further comprises a lead breach extending between proximal and distal guide body tracking lumen end openings normally having a narrow breach width when said lead body is clamped to cause said lead engaging means to tightly bear against said lead body and wherein said releasing means comprises means for widening said lead breach to a wide breach width to release said lead body to allow said lead engaging means to be withdrawn proximally along said lead body upon expansion of said balloon.

* * * * *